US011158425B2

(12) United States Patent
Futscher de Deus et al.

(10) Patent No.: US 11,158,425 B2
(45) Date of Patent: *Oct. 26, 2021

(54) SYSTEM AND METHOD FOR MANAGING GENOMIC INFORMATION

(71) Applicant: FOUNDATION MEDICINE, INC., Cambridge, MA (US)

(72) Inventors: Helena Futscher de Deus, Cambridge, MA (US); Rachel Lauren Erbach, Arlington, MA (US); Ronald David Collette, Dove Canyon, CA (US); Alexander N. Parker, Boston, MA (US); Michael Pellini, Dana Point, CA (US); Gary Palmer, Waltham, MA (US); Mary Pat Lancelotta, Somerville, MA (US); Matthew J. Hawryluk, Watertown, MA (US); Philip James Stephens, Lexington, MA (US); Eric Karl Neumann, Cambridge, MA (US)

(73) Assignee: FOUNDATION MEDICINE, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/463,068

(22) Filed: Aug. 19, 2014

(65) Prior Publication Data

US 2015/0046180 A1 Feb. 12, 2015

Related U.S. Application Data

(63) Continuation-in-part of application No. 14/146,743, filed on Jan. 3, 2014, now abandoned.

(60) Provisional application No. 61/749,288, filed on Jan. 5, 2013, provisional application No. 61/749,291, filed on Jan. 5, 2013.

(51) Int. Cl.
| | |
|---|---|
| *G16H 50/20* | (2018.01) |
| *G16H 10/60* | (2018.01) |
| *G16C 99/00* | (2019.01) |
| *G16H 10/20* | (2018.01) |
| *G16H 10/40* | (2018.01) |
| *G16H 70/60* | (2018.01) |
| *G16H 15/00* | (2018.01) |

(52) U.S. Cl.
CPC ............ *G16H 50/20* (2018.01); *G16C 99/00* (2019.02); *G16H 10/20* (2018.01); *G16H 10/40* (2018.01); *G16H 10/60* (2018.01); *G16H 70/60* (2018.01); *G16H 15/00* (2018.01)

(58) Field of Classification Search
None
See application file for complete search history.

(56) References Cited

U.S. PATENT DOCUMENTS

| | | |
|---|---|---|
| 7,353,238 B1 | 4/2008 | Gliklich |
| 2002/0052761 A1 | 5/2002 | Fey et al. |
| 2003/0046114 A1 | 3/2003 | Davies et al. |
| 2003/0113756 A1 | 6/2003 | Mertz |
| 2004/0078236 A1 | 4/2004 | Stoodley et al. |
| 2005/0026117 A1 | 2/2005 | Judson et al. |
| 2005/0261941 A1 | 11/2005 | Scarlat |
| 2006/0004526 A1 | 1/2006 | Hadd et al. |
| 2008/0161661 A1 | 7/2008 | Gizewski |
| 2008/0201172 A1 | 8/2008 | McNamar |
| 2009/0080734 A1 | 3/2009 | Moriya et al. |
| 2009/0287503 A1 | 11/2009 | Angell et al. |
| 2010/0131293 A1 | 5/2010 | Linthicum et al. |
| 2010/0218132 A1 | 8/2010 | Soni et al. |
| 2012/0157340 A1 | 6/2012 | Cesano et al. |

(Continued)

FOREIGN PATENT DOCUMENTS

| | | |
|---|---|---|
| KR | 20110097889 A | 8/2011 |
| WO | WO-2012059839 A2 | 5/2012 |

(Continued)

OTHER PUBLICATIONS

S. Yilmaz et al. Gene-disease relationship discovery based on model-driven data integration and database view definition, Bioinformatics, vol. 25, Issue 2, Jan. 15, 2009, pp. 230-236, https://doi.org/10.1093/bioinformatics/btn612.*

(Continued)

*Primary Examiner* — Joseph Woitach

(74) *Attorney, Agent, or Firm* — Morrison & Foerster LLP

(57) ABSTRACT

Various embodiments provide interfaces to access genomic testing information and incorporate it into daily physician practice. According to one aspect, a graph-based data model is used that may be used to organizes and revise precision medicine knowledge. In one example structure, gene states are abstracted into alteration groups, where alteration groups are built using reverse engineering actionable information and storing that information within the graph-based data structure. Volumes of genomic alterations and associated information (e.g., journal articles, clinical trial information, therapies, etc.) are analyzed and synthesized into actionable information items viewable on an alteration system in a graph-based data format. According to one embodiment, the system can be configured to focus practitioners on discrete portions of the alteration information on which they can act. According to other aspects, curated information is provided on the system to enable practitioners to make informed decisions regarding the implications of the presence of specific genomic alterations.

46 Claims, 21 Drawing Sheets

(56) References Cited

U.S. PATENT DOCUMENTS

| | | | |
|---|---|---|---|
| 2014/0336943 A1 | 11/2014 | Pellini et al. |
| 2014/0337052 A1 | 11/2014 | Pellini et al. |
| 2015/0046191 A1 | 2/2015 | de Deus et al. |
| 2016/0103973 A1 | 4/2016 | Singal et al. |
| 2020/0020430 A1 | 1/2020 | de Deus et al. |
| 2020/0020452 A1 | 1/2020 | de Deus et al. |
| 2020/0211679 A1 | 7/2020 | Pellini et al. |
| 2020/0294668 A1 | 9/2020 | Pellini et al. |

FOREIGN PATENT DOCUMENTS

| | | | |
|---|---|---|---|
| WO | WO-2012059839 A2 | 6/2012 |
| WO | 2014107549 A2 | 7/2014 |

OTHER PUBLICATIONS

Haga et al., "Developing patient-friendly genetic and genomic test reports formats to promote patient engagement and understanding" genome Medicine (2014) vol. 6 No. 58 pp. 1-11.
"Graph Database—Wikipedia" Dec. 7, 2014; Retrieved from the internet on Jun. 26, 2018; URL: https://en.wikipedia.org/w/index.php?title=Graph_database&oldId=637006716.
Extended European Search Report and Opinion for European Application No. 20201144.1 dated Mar. 30, 2021, 11 pages.
European Supplementary Search Report for European Application No. 14735224.9 dated Jul. 6, 2016, 8 pages.
Extended European Search Report and Opinion for European Application No. 15833420.1 dated Mar. 15, 2018, 12 pages.
Extended European Search Report and Opinion for European Application No. 15871055.8 dated Jul. 27, 2018, 11 pages.
International Search Report for PCT/US2014/010124; dated May 8, 2014, 3 pages.
International Search Report for PCT/US2014/010125; dated Jun. 24, 2014, 5 pages.
International Search Report for PCT/US2015/045859; dated Nov. 24, 2015, 4 pages.
International Search Report for PCT/US2015/066325; dated Apr. 7, 2016, 3 pages.
U.S. Appl. No. 16/793,405, filed Feb. 18, 2020, by inventor Pellini et al., titled "system and method for managing genomic testing results." (Copy not submitted herewith pursuant to the waiver of 37 C.F.R. § 1.98(a)(2)(iii)).
Written Opinion of the International Searching Authority for PCT/US2015/045859 dated Nov. 24, 2015, 11 pages.
Written Opinion of the International Searching Authority for PCT/US2015/066325 dated Apr. 7, 2016, 6 pages.
Barabasi et al "Network medicine: a network approach to human disease" Nature Reviews Genetics (2011) vol. 12 No. 1 pp. 56-68.
Bebek et al, "Network biology methods integrating biological data for translational science" Briefings in Bioinformatics (2012) vol. 13, No. 4 pp. 446-459.
Chun et al., "A network perspective on unraveling the role of TRP channels in biology and disease" Pflugers Archiv—european Journal of Physiology (2014) vol. 446 No. 2 pp. 173-182.

* cited by examiner

```
CONSTRUCT {
    ?newdta a DTA; ;
        hasTherapy: ?Therapy ;
        hasDisease: ?Disease ;
        hasFdaStatus: ?FDAStatus .
}
WHERE {
    ?dta a DTA; ;
        hasTherapy: ?Therapy ;
        hasDisease: ?BroaderDisease;
        hasFdaStatus: ?FDAStatus .
    ?BroaderDisease skos:narrower+ ?Disease .
}
```

Figure 9

SYSTEM AND METHOD FOR MANAGING GENOMIC INFORMATION

RELATED APPLICATIONS

This application is a continuation-in-part of U.S. application Ser. No. 14/146,743, entitled SYSTEM AND METHOD FOR MANAGING GENOMIC TESTING RESULTS, filed Jan. 3, 2014 which is a non-provisional application of and claims priority under 35 U.S.C. § 119(e) to U.S. Provisional App. No. 61/749,291, entitled "SYSTEM AND METHOD FOR MANAGING GENOMIC TESTING RESULTS," filed Jan. 5, 2013, and U.S. Provisional App. No. 61/749,288, entitled "SYSTEM AND METHOD FOR OUTCOME TRACKING AND ANALYSIS," filed Jan. 5, 2013, of which applications are incorporated herein by reference by their entirety.

BACKGROUND

Genomic testing of cancer cells shows significant promise towards developing better understanding of cancers and managing more effective treatment approaches. Genomic testing involves the sequencing of the genome of a patient's cancer cells and identifying any genomic alteration in those cells. A genomic alteration can include, for example, mutations, deleted gene sequences, amplifications, translocation, among other options. Understanding these genomic alterations as they are found in a specific patient's cancer may also help develop better treatments and help identify the best approaches for treating specific cancer variants using genomic alteration information.

SUMMARY

It is realized that the adoption and integration of genomic testing into daily practice faces significant hurdles, in part, based on the ability to access and the volume of the information that needs to be reviewed and understood in order to facilitate treatment decisions. Further, the complexity of the genomic analysis has also limited its potential and in some cases limited implementation. It is also realized that conventional approaches for providing genomic alteration information are not readily appreciated by the majority of practitioners for their diagnostic value. Nor can the majority of practitioners incorporate such information into actionable steps to be taken with a given patient, or identify clinically relevant information.

According to one aspect, it is realized that in order to effectively incorporate genomic testing information into daily physician practice, genomic alteration data must be simplified and/or coupled with contextual applications of the genomic alteration data. In some embodiments, volumes of genomic alterations and associated information (e.g., journal articles, clinical trial information, therapies, etc.) are analyzed and synthesized into actionable or clinically relevant information items viewable on an alteration system. According to one embodiment, the system can be configured to focus practitioners on discrete portions of the alteration information on which they can act or receive meaningful information.

According to one aspect of the present invention, it is appreciated that many systems exist that may be used in an attempt to determine and identify patterns in diseases, however, many of these systems fail due to the amount of data available. In particular, it is appreciated that the challenge of precision medicine from a knowledge engineering standpoint is two-fold. First, there is a large number of gene state/disease subtype associations that are available. The numbers of associations can make the problem of discovering an actionable solution or clinically relevant information intractable and not computable. However, knowledge associations are not static. For instance, with new discoveries, the set of knowledge upon which an actionable item may be determined changes. Knowledge organization systems that are capable of providing up to date actionable information should be flexible to accommodate those changes.

According to one aspect of the present invention, it is realized that a graph-based model may be used for organizing and revising precision medicine knowledge. According to one embodiment, the problem to be solved includes discovering actionable items given patient context items. In one embodiment, actionable items include applying therapies to a patient and performing clinical trials. Patient context items may include disease phenotype and genetic alterations.

One novel aspect includes an abstraction of gene states into alterations groups (AGs). According to one implementation, a method for building AGs relies on reverse engineering actionable information and storing that information within the graph-based representation.

Precision or personalized medicine is an approach to medicine that makes use of genomic, epigenomic, environmental exposure and other available data types to define individual patterns of disease. The promise behind a comprehensive and holistic approach to medicine is that better individual and objectified medicine will be enabled. Precision medicine is also at the core of a paradigm shift in the way medical knowledge engineering, organization and analysis are carried out.

Consider the following: the number of biomedical databases increases every year, with the latest issue of NAR reporting 1552 high quality databases on its online molecular biology database collection; the number of medical and biological reference papers representative of medically relevant discoveries indexed by Pubmed increases by about one per minute; the price of raw sequencing of the human genome is dropping faster than Moore's law, leading to a significant increases in the accessibility of genomic data and bioinformatics algorithms everyday predict novel protein structures and malignancies from raw sequence data, multiplying the amount of data available to the physicians willing to learn from it. This is the era of "big data" for biomedical progress—this data has all the properties that make it so.

Consider now a physician trying to use a computer system to obtain the answer to an apparently simple question: "Will my patient respond to this drug?" Being able to support this type of precise, often quantitative query (e.g. what dose of the treatment will the patient tolerate/respond to), would require an infrastructure that is "aware" of which variables contribute to the patient's response, namely the patients' individual genetic make-up (and the diseased cells), the pharmacodynamics aspect that predicts how the drug will degrade/leave the organism based on its chemical properties and often financial aspects such as the price of a particular therapy when weighted against its benefit for the patient. Fortunately, for many diseases, patients do respond more or less homogeneously and the treatment does not easily accumulate to toxic levels.

However, when one considers long-tail diseases like cancer, which is driven by a variety of different genomic aberrations and is often a combination of the activation of oncogenes and inactivation of tumor suppressors, combined with a high heterogeneity in the response to treatment, the answer often requires quantitative precision and predicting—often with incomplete data—how complex dynamic interactions between drug and proteins will affect phenotype. Being unable to systematically provide an answer to precision medicine questions has been a major bottleneck to the application of precision medicine—and major source of frustrations for an increasing number of scientists, who have summarized it in the well-known expression "data, data everywhere, not a drop of value."

Traditional approaches have involved the use of relational types of databases, however, it is appreciated that there are many drawbacks associated with using traditional forms of data storage. First, the data sizes being observed are typically very large considering all of the numbers of sources available. Another constraint includes the homogeneity and sparseness of the data, making the relational database unsuitable—rather, a decision-based model may be more appropriate. Also, the storage of semantic information in a relational model is not conducive to conventional relational models—many times, it is appreciated that in such conventional models, information is either lost or data does not propagate through the relations when updated. For instance, the relational model does not organize pathologies as hierarchies that support propagation of information (e.g., FDA approval for a class of cancers that fall in a similar hierarchy). Because, in some relational models, hierarchies are flattened, some information context is lost.

According to aspect of the present invention, a graph model that implements a tuple of information may be used to determine actionable items. Each tuple may include at least two elements connected by a relation. For instance, a patient element representing an individual patient may be connected to a particular cancer through a diagnosis relation. In another example, a gene state may be connected to a treatment by an inactivation relation.

In one embodiment, the graph model includes an abstraction of gene states into alteration groups (AGs). In one embodiment, an inference engine may be provided that analyzes biomarkers for a given patient to determine treatment decisions. For instance, biomarker information combined with the patient's specific pathology provide information regarding the patient's susceptibility or resistance to a particular set of therapies and/or whether the patient is eligible to enroll in a clinical trial. In one implementation, information regarding the biomarkers and patient information may be organized into tuples, and the tuples may be organized into a walkable graph that leads to action items.

In another embodiment, tuples and their relations may include a measurement of trust in each link of the tuple. In one embodiment, the quality of the information along a particular path may be an accumulation of trust scores along the path. In one implementation, a final trust in an answer may be computed by multiplying trust scores of each path or connection followed to derive a particular answer.

According to other aspects, curated information is provided on the system to enable practitioners to make informed decisions regarding the implications of the presence of specific genomic alterations. Curated information includes interpretations of available information (e.g., existing therapies, clinical trials, journals, and publications) for genomic alterations that may be found in a patient's tumor as a result of the genomic analysis. The genomic analysis can identify, for example, a tumor type, an affected gene, and an alteration type specific to a given patient and their cancer. The available information that can be curated can be associated with, and organized by, any of the information provided in the genomic analysis (e.g., specific to tumor type, gene, and alteration).

According to one embodiment, the interpretations present contextual information regarding the gene implicated in a patient's cancer, including, for example, the expression of the gene, related genes, and can provide information on related therapies or clinical trials. In some embodiments, the curated information can also include interpretive statements that summarize and/or apply current analysis of any available information associated with genomic alterations (including, for example, information on an identified gene, information on an identified alteration, and information on the patient's tumor). Further, the curated information can be integrated into a display with genomic test results, providing intuitive and easy access information sources for understanding implication of the test results. Additionally, the curated information can include references to an information source from which the curated information is derived. In some embodiments, the system can provide direct access to a source of the curated information. For example, the system can provide for direct navigation to a relevant clinical trial while in context of reviewing information on a specific genomic alteration. The curated information can also include direct links to the source information hosted at external information sites. (e.g., ClinicalTrials.gov, PubMed, etc.). The information sources can also be reviewed by the user to further describe or validate the curated information being provided.

By providing such curated information with an easily navigable interface, a physician or other health care provider may locate the best treatment information in a timely manner. In some embodiments, the interface can be organized and navigated based on specific alterations found in a patient's cancer. In such settings, the user can navigate to information matching the patient's cancer (e.g., tumor type, gene, and alteration) to find directly relevant treatment information. Additionally, the user can navigate to related information matching one or more of a patient's tumor type, gene, and alteration to inform the user of potential off-label treatment options.

According to another aspect, provided are systems and methods for managing genomic testing information that provide a single reporting source for accessing and applying available information on a patient's cancer. According to some embodiments, genomic testing on the patient's cancer provides specific information on the tumor, one or more genes implicated by the tumor, and one or more alterations within the genes. The testing information on tumor, gene, and alteration can be used by the system to manage delivery of curated information that focuses users (e.g., physicians) on actionable information within the genomic testing information. For example, publically available data (e.g., therapy data, clinical trial data, and journal publications) can be interpreted to provide the curated information. The curated information can be accessed on the system based on its relationship to one or more of the tumor, gene, and alteration for a patient. The publically available information can also be processed on the system to provide navigable data structures informing the user of available actionable information associated with a patient's cancer.

In further aspects, the practitioner is able to view the single report source for genomic information on the system. The single report source can incorporate tumor information, gene information, and genomic alteration information to review and, potentially, to apply actionable steps towards treating various cancers. According to one embodiment, the single report source is dynamic, incorporating updates to any associated information (e.g., new curated information, updated curated information, a new clinical trial, a new therapy, a new publication associated with any of an alteration, gene, tumor found in a genomic test report) as they become available. The system can deliver update notifications responsive to new information. Further embodiments provide intuitive navigation options within views on the system to expand the information displayed and/or navigate to additional information on a selected information source (e.g., specific information on a tumor, gene, and/or alteration, and external links to available information, among other options).

According to one embodiment, a user interface is provided that allows easy navigation to genomic alteration results and associated information to reduce the amount of time necessary to determine an appropriate treatment for a user. For instance, as a result of genomic testing, of a patient sample, particular genomic alterations may be detected and displayed to a user for a particular patient. The user may be presented, within the display, a collection of information that user would need to access to provide an informed treatment recommendation. For instance, with a first level view of identified alterations, the user may be permitted to navigate to other information related to the genomic alterations, such as, therapy information, information on a clinical trial related to the genomic alteration, and any references that might be available to inform or support the application of such therapies. By having such information within an easily navigable interface, users may more quickly identify appropriate treatments.

According to one embodiment, the system may identify and display to the user genomic alterations and associated information arranged based on actionability analysis. The actionability analysis can be configured to display genomic alteration and associated information having the highest degree of actionability. In one embodiment, the actionability analysis can prioritize information on available therapies or related therapies over clinical trial information and available references. Additionally, the clinical trial information can be prioritized over available references. The priority can be used by the system to define display precedence. For example, an order of display for genomic alterations and associated information can reflect the priority and/or actionability analysis.

In some embodiments, the system can provide an indication regarding the number or volume of therapy information items, the number or volume or clinical information items, and the number or volume of available reference information items. The numbers within each group can also be used to establish priority. For example, on genomic alterations having multiple associate therapies, the alteration having the larger number can be displayed first. As updates to genomic alterations and associated information occur, the actionability analysis can change over time to reflect the new information. Further, such updates can be communicated directly to the user and/or highlighted in a test report for the user's review.

According to another aspect, the system can be organized based on a genomic testing data model. In one embodiment, the data model is configured to organize information on tumor type, implicated genes within the tumor, and alteration types for the implicated genes for specific tests and/or by patient. The system is configured to use the data model to facilitate access to genomic alteration test results and all related information for a test and/or patient. In some embodiments, the gene/alteration combination can form at least part of the basis of organization. Each gene/alteration combination can be linked in the data model to actionable information and/or clinically relevant information (if any exists). In one embodiment, the actionable information and/or clinically relevant information can be linked to any of the gene/alteration combinations and, in one embodiment, must be matched to the tumor type for a patient. Categorization of all information in the data model by associating a gene, alteration, and/or tumor type provides insight into prescribed uses of therapies (on-label) and off-label applications based on related alteration information (e.g., information on different tumors but the same alteration—an effective therapy for the alteration in a different tumor type could be relevant to a patient's tumor type).

In some embodiments, users are able to share test reports and associated information between physicians in a practice group or between physicians within an institution (e.g., hospital, treatment facility, etc.) In addition to the dynamic display of the genomic information and associated information, some embodiments, of the system can provide for generation of physical and/or static reports. In one example, a physical report can be generated to include genomic alteration information for a patient and all the associated information organized into display groups for therapy, trial, and reference information.

According to one aspect, a system for managing delivery of genomic information is provided. The system comprises at least one processor operatively connected to a memory, the at least one processor when executing is configured to collecting biomarker data and storing the biomarker data in the memory; receiving patient-specific pathology information relating to a patient and storing the patient-specific pathology information in the memory; determining a graph-based data structure that includes the biomarker data and the patient-specific pathology information; and determining one or more actionable items within the graph-based data structure responsive to the biomarker data and patient-specific pathology information.

In one embodiment, the actionable items includes at least one of a group comprising a recommendation for an enrollment of the patient in a clinical trial and a recommendation for a therapy to be applied to the patient. In another embodiment, the patient-specific pathology information relating to the patient includes at least one of a group comprising disease phenotype information and genetic alteration information.

In another embodiment, the graph-based data structure includes information organized into a plurality of tuples of information. In one embodiment, each of the plurality of tuples of information include at least two elements connected by a relation. In one embodiment, at least one of the plurality of tuples includes a patient identifier connected to a particular disease through a diagnosis relation. In one embodiment, at least one of the plurality of tuples includes a gene state connected to a treatment type by an inactivation relation.

In one embodiment, at least one of the plurality of tuples includes information generated as a result of a genomic test report. In one embodiment, at least one of the plurality of tuples includes information generated as a result of a clinical study. In one embodiment, at least one of the plurality of tuples includes an alteration group (AG) and an actionable element. In one embodiment, at least one of the plurality of tuples includes a disease and an alteration group (AG).

In one embodiment, the plurality of tuples are organized by the system into a walkable graph representation. In one embodiment, at least one of the plurality of tuples includes a trust score. In one embodiment, the trust score is provided that indicates the likelihood of following an inferred path in graph-based data structure. In one embodiment, trust scores for multiple paths in the graph-based data structure are used to determine one or more actionable items. In one embodiment, the act of determining one or more actionable items within the graph-based data structure responsive to the biomarker data and patient-specific pathology information is performed by an inference engine.

In one embodiment, the graph-based data structure includes an abstraction of gene states into alteration groups (AGs). In one embodiment, the at least one processor when executing is configured to provide an output of the one or more actionable items to a user of the system. In one embodiment, the graph-based data structure includes the resource description framework model (RDF). In one embodiment, the graph-based data structure includes actionable items as leaf nodes. In one embodiment, the graph-based data structure includes actionable items as a function of one or more context items. In one embodiment, the one or more context items include a disease, a gene, and an alteration.

In one embodiment, the actionable items includes at least one of a group comprising a recommendation for an enrollment of the patient in a clinical trial and a recommendation for a therapy to be applied to the patient. In one embodiment, the graph-based data structure includes a plurality of complex data elements. In one embodiment, at least one of the plurality of complex data elements includes a text node element that stores information relevant for precision medicine decision making with respect to a referenced element of the graph-based data structure.

In one embodiment, the graph-based data structure includes an alteration group (AG) comprising a plurality of gene states. In one embodiment, each of the plurality of gene states belongs to a single AG. In one embodiment, the AG comprises a combination of attributes that defines a unique set of clinically relevant gene states. In one embodiment, at least one of the plurality of complex data elements includes a disease alteration group association (DAGA) element. In one embodiment, the disease alteration group association (DAGA) element represents a relationship between a disease and an alteration group (AG). In one embodiment, the disease alteration group association (DAGA) element associates the disease and alteration group (AG) with one or more actionable elements. In one embodiment, at least one of the plurality of complex data elements includes a disease therapy association (DTA) element that associates a disease and a therapy with information relevant to the combination of the disease and the therapy. In one embodiment, at least one of the plurality of complex data elements includes a therapy genomic effect (TGE) element that associates a gene targeted by a therapy and a known effect of the therapy.

In one embodiment, the at least one processor when executing is configured to propagate information within the graph-based data structure that includes the biomarker data and the patient-specific pathology information. In one embodiment, the at least one processor when executing is configured to propagate FDA approval status within a disease ontology tree associated with the graph-based data structure. In one embodiment, the at least one processor when executing is configured to infer relations within the graph-based data structure based on one or more propagation rules. In one embodiment, the at least one processor when executing is configured to merge gene states having shared actionability items into a single alteration group (AG) element. In one embodiment, the at least one processor when executing is configured to merge more than one DAGA element that shares actionability items.

According to one aspect, a computer-implemented method for managing delivery of genomic information is provided. The method comprises acts of collecting, by a computer system having a memory, biomarker data and storing the biomarker data in the memory; receiving, by the computer system, patient-specific pathology information relating to a patient and storing the patient-specific pathology information in the memory; determining a graph-based data structure that includes the biomarker data and the patient-specific pathology information; and determining, by the computer system, one or more actionable items within the graph-based data structure responsive to the biomarker data and patient-specific pathology information.

In one embodiment, the actionable items includes at least one of a group comprising a recommendation for an enrollment of the patient in a clinical trial and a recommendation for a therapy to be applied to the patient. In another embodiment, the patient-specific pathology information relating to the patient includes at least one of a group comprising disease phenotype information and genetic alteration information.

In another embodiment, the graph-based data structure includes information organized into a plurality of tuples of information. In one embodiment, each of the plurality of tuples of information include at least two elements connected by a relation. In one embodiment, at least one of the plurality of tuples includes a patient identifier connected to a particular disease through a diagnosis relation. In one embodiment, at least one of the plurality of tuples includes a gene state connected to a treatment type by an inactivation relation.

In one embodiment, at least one of the plurality of tuples includes information generated as a result of a genomic test report. In one embodiment, at least one of the plurality of tuples includes information generated as a result of a clinical study. In one embodiment, at least one of the plurality of tuples includes an alteration group (AG) and an actionable element. In one embodiment, at least one of the plurality of tuples includes a disease and an alteration group (AG).

In one embodiment, the method, further comprises an act of organizing, by the computer system, the plurality of tuples into a walkable graph representation. In one embodiment, at least one of the plurality of tuples includes a trust score. In one embodiment, the method further comprises an act of providing the trust score that indicates the likelihood of following an inferred path in graph-based data structure. In one embodiment, the act of determining the one or more actionable items includes evaluating trust scores for multiple paths in the graph-based data structure. In one embodiment, the act of determining one or more actionable items within the graph-based data structure responsive to the biomarker data and patient-specific pathology information is performed by an inference engine.

In one embodiment, the graph-based data structure includes an abstraction of gene states into alteration groups (AGs). In one embodiment, the method further comprises an act of providing an output of the one or more actionable items to a user of the computer system. In one embodiment, the graph-based data structure includes the resource description framework model (RDF). In one embodiment, the graph-based data structure includes actionable items as leaf nodes. In one embodiment, the graph-based data structure includes actionable items as a function of one or more context items. In one embodiment, the one or more context items include a disease, a gene, and an alteration.

In one embodiment, the actionable items includes at least one of a group comprising a recommendation for an enrollment of the patient in a clinical trial and a recommendation for a therapy to be applied to the patient. In one embodiment, the graph-based data structure includes a plurality of complex data elements. In one embodiment, at least one of the plurality of complex data elements includes a text node element that stores information relevant for precision medicine decision making with respect to a referenced element of the graph-based data structure.

In one embodiment, the graph-based data structure includes an alteration group (AG) comprising a plurality of gene states. In one embodiment, each of the plurality of gene states belongs to a single AG. In one embodiment, the AG comprises a combination of attributes that defines a unique set of clinically relevant gene states. In one embodiment, at least one of the plurality of complex data elements includes a disease alteration group association (DAGA) element. In one embodiment, the method further comprises an act of representing, by the disease alteration group association (DAGA) element, a relationship between a disease and an alteration group (AG). In one embodiment, the method further comprises an act of associating, by the disease alteration group association (DAGA) element, the disease and alteration group (AG) with one or more actionable elements. In one embodiment, at least one of the plurality of complex data elements includes a disease therapy association (DTA) element that associates a disease and a therapy with information relevant to the combination of the disease and the therapy. In one embodiment, at least one of the plurality of complex data elements includes a therapy genomic effect (TGE) element that associates a gene targeted by a therapy and a known effect of the therapy.

In one embodiment, the method further comprises an act of propagating, by the computer system, information within the graph-based data structure that includes the biomarker data and the patient-specific pathology information. In one embodiment, the method further comprises an act of propagating, by the computer system, FDA approval status within a disease ontology tree associated with the graph-based data structure. In one embodiment, the method, further comprises an act of inferring, by the computer system, relations within the graph-based data structure based on one or more propagation rules. In one embodiment, the method further comprises an act of merging, by the computer system, gene states having shared actionability items into a single alteration group (AG) element. In one embodiment, the method further comprises an act of merging, by the computer system, more than one DAGA element that shares actionability items.

According to one aspect, a system for managing delivery of genomic information is provided. The system comprises at least one processor operatively connected to a memory, the at least one processor when executing is configured to collect biomarker data and storing the biomarker data in the memory; receive patient-specific pathology information relating to a patient and storing the patient-specific pathology information in the memory; and determine a graph-based data structure that includes the biomarker data and the patient-specific pathology information wherein the graph-based data structure includes an alteration group (AG) comprising a plurality of gene states.

In one embodiment, the at least one processor when executing is configured to determine one or more actionable items within the graph-based data structure responsive to the biomarker data and patient-specific pathology information. In one embodiment, the graph-based data structure includes a plurality of complex data elements.

In one embodiment, each of the plurality of gene states belongs to a single AG. In one embodiment, the AG comprises a combination of attributes that defines a unique set of clinically relevant gene states. In one embodiment, at least one of the plurality of complex data elements includes a disease alteration group association (DAGA) element. In one embodiment, the disease alteration group association (DAGA) element represents a relationship between a disease and the (AG).

In one embodiment, the disease alteration group association (DAGA) element associates the disease and the alteration group (AG) with one or more actionable elements. In one embodiment, the actionable items includes at least one of a group comprising a recommendation for an enrollment of the patient in a clinical trial and a recommendation for a therapy to be applied to the patient. In one embodiment, the patient-specific pathology information relating to the patient includes at least one of a group comprising disease phenotype information and genetic alteration information.

In one embodiment, the graph-based data structure includes information organized into a plurality of tuples of information. In one embodiment, each of the plurality of tuples of information include at least two elements connected by a relation. In one embodiment, at least one of the plurality of tuples includes a patient identifier connected to a particular disease through a diagnosis relation. In one embodiment, at least one of the plurality of tuples includes a gene state connected to a treatment type by an inactivation relation.

In one embodiment, at least one of the plurality of tuples includes information generated as a result of a genomic test report. In one embodiment, at least one of the plurality of tuples includes information generated as a result of a clinical study. In one embodiment, at least one of the plurality of tuples includes an alteration group (AG) and an actionable element. In one embodiment, at least one of the plurality of tuples includes a disease and an alteration group (AG).

In one embodiment, the plurality of tuples are organized by the system into a walkable graph representation. In one embodiment, at least one of the plurality of tuples includes a trust score. In one embodiment, the trust score is provided that indicates the likelihood of following an inferred path in graph-based data structure. In one embodiment, trust scores for multiple paths in the graph-based data structure are used to determine one or more actionable items. In one embodiment, the graph-based data structure includes the resource description framework model (RDF). In one embodiment, the graph-based data structure includes actionable items as leaf nodes. In one embodiment, the graph-based data structure includes actionable items as a function of one or more context items. In one embodiment, the one or more context items include a disease, a gene, and an alteration.

In one embodiment, the graph-based data structure includes a plurality of complex data elements. In one embodiment, at least one of the plurality of complex data elements includes a text node element that stores information relevant for precision medicine decision making with respect to a referenced element of the graph-based data structure. In one embodiment, at least one of the plurality of complex data elements includes a disease therapy association (DTA) element that associates a disease and a therapy with information relevant to the combination of the disease and the therapy. In one embodiment, at least one of the plurality of complex data elements includes a therapy genomic effect (TGE) element that associates a gene targeted by a therapy and a known effect of the therapy. In one embodiment, the at least one processor when executing is configured to merge gene states having shared actionability items into a single alteration group (AG) element. In one embodiment, the at least one processor when executing is configured to merge more than one DAGA element that shares actionability items.

According to one aspect, a method for managing delivery of genomic information is provided. The method comprising acts of collecting, by a computer system having a memory, biomarker data and storing the biomarker data in the memory; receiving patient-specific pathology information relating to a patient and storing the patient-specific pathology information in the memory; and determining a graph-based data structure that includes the biomarker data and the patient-specific pathology information wherein the graph-based data structure includes an alteration group (AG) comprising a plurality of gene states. In one embodiment, the method, further comprises an act of determining, by the computer system, one or more actionable items within the graph-based data structure responsive to the biomarker data and patient-specific pathology information. In one embodiment, the graph-based data structure includes a plurality of complex data elements.

In one embodiment, each of the plurality of gene states belongs to a single AG. In one embodiment, the AG comprises a combination of attributes that defines a unique set of clinically relevant gene states. In one embodiment, at least one of the plurality of complex data elements includes a disease alteration group association (DAGA) element. In one embodiment, the disease alteration group association (DAGA) element represents a relationship between a disease and the (AG).

In one embodiment, the disease alteration group association (DAGA) element associates the disease and the alteration group (AG) with one or more actionable elements. In one embodiment, the actionable items includes at least one of a group comprising a recommendation for an enrollment of the patient in a clinical trial and a recommendation for a therapy to be applied to the patient. In one embodiment, the patient-specific pathology information relating to the patient includes at least one of a group comprising disease phenotype information and genetic alteration information.

In one embodiment, the graph-based data structure further comprising an act of organizing information into a plurality of tuples of information. In one embodiment, each of the plurality of tuples of information include at least two elements connected by a relation. In one embodiment, at least one of the plurality of tuples includes a patient identifier connected to a particular disease through a diagnosis relation. In one embodiment, at least one of the plurality of tuples includes a gene state connected to a treatment type by an inactivation relation.

In one embodiment, at least one of the plurality of tuples includes information generated as a result of a genomic test report. In one embodiment, at least one of the plurality of tuples includes information generated as a result of a clinical study. In one embodiment, at least one of the plurality of tuples includes an alteration group (AG) and an actionable element. In one embodiment, at least one of the plurality of tuples includes a disease and an alteration group (AG).

In one embodiment, the method further comprises an act of organizing, by the computer system, the plurality of tuples into a walkable graph representation. In one embodiment, at least one of the plurality of tuples includes a trust score. In one embodiment, the method further comprises an act of providing the trust score indicating a likelihood of following an inferred path in graph-based data structure. In one embodiment, the method further comprises an act of determining, by the computer system, the one or more actionable items wherein trust scores for multiple paths in the graph-based data structure are used to determine one or more actionable items. In one embodiment, the graph-based data structure includes the resource description framework model (RDF). In one embodiment, the graph-based data structure includes actionable items as leaf nodes. In one embodiment, the graph-based data structure includes actionable items as a function of one or more context items. In one embodiment, the one or more context items include a disease, a gene, and an alteration.

In one embodiment, the graph-based data structure includes a plurality of complex data elements. In one embodiment, at least one of the plurality of complex data elements includes a text node element that stores information relevant for precision medicine decision making with respect to a referenced element of the graph-based data structure. In one embodiment, at least one of the plurality of complex data elements includes a disease therapy association (DTA) element that associates a disease and a therapy with information relevant to the combination of the disease and the therapy. In one embodiment, at least one of the plurality of complex data elements includes a therapy genomic effect (TGE) element that associates a gene targeted by a therapy and a known effect of the therapy. In one embodiment, the method further comprises an act of merging, by the computer system, gene states having shared actionability items into a single alteration group (AG) element. In one embodiment, the method further comprises an act of merging, by the computer system, more than one DAGA element that shares actionability items.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed below with reference to the accompanying figures, which are not intended to be drawn to scale. Where technical features in the figures, detailed description or any claim are followed by reference signs, the reference signs have been included for the sole purpose of increasing the intelligibility of the figures, detailed description, and claims. Accordingly, neither the reference signs nor their absence, are intended to have any limiting effect on the scope of any claim elements. In the figures, each identical or nearly identical component that is illustrated in various figures is represented by a like numeral. For purposes of clarity, not every component may be labeled in every figure. The figures are provided for the purposes of illustration and explanation and are not intended as a definition of the limits of the invention. In the figures:

FIG. 9 shows an example query according to one embodiment of the present invention;

DETAILED DESCRIPTION

As discussed above, unique data models may be used to facilitate the processing of genomic information. Such an information model may be used by a tool (e.g., a computer-based tool) to store and analyze genomic information in such a way that may enable users (e.g., physicians, oncologists, or other user types) to assimilate large amounts of information relating to patients, gene state, disease and treatment information, among other types, to produce a system that is capable of determining actionable items in relation to this data.

As discussed, a graph model may be used to analyze biomarker data and patient data to determine actionable items. Graph models differ from relational data models in several respects in that they make relations between data elements explicit (i.e., each relationship has a name for an identifier) and they represent information as a list of connections (e.g., as tuples, or triples (at least two items connected by a relationship)).

Figure 1:
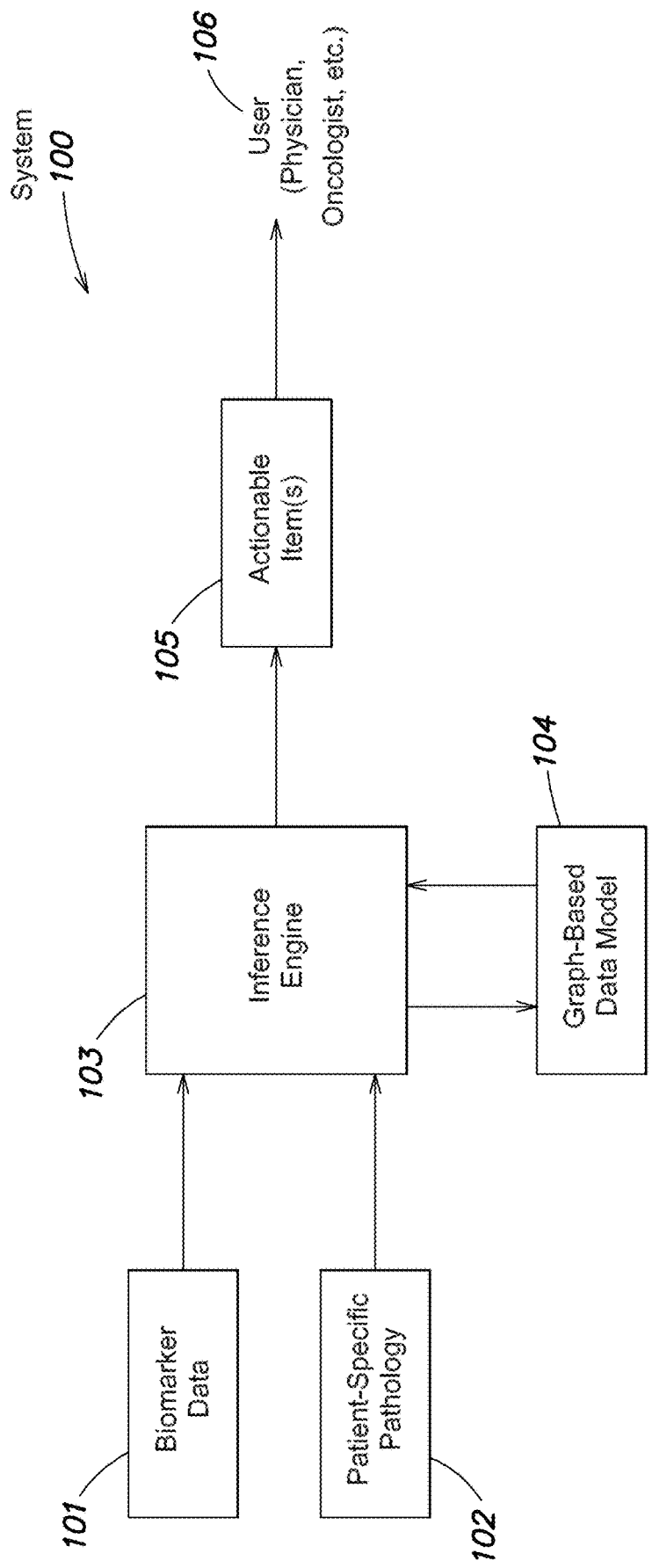
FIG. 1 is block diagram showing an inference engine according to one embodiment of the present invention.

FIG. 1 shows a system 100 which may include one or more computer-based systems that receive and collect biomarker data 101 and patient specific pathology information 102. System 100 includes an inference engine 103 that interprets a graph-based data model 104 to determine one or more actionable items 105. Such actionable items may be presented to a user 106 (e.g. a physician, oncologists, or other user type). Such actionable items may include recommending a patient for clinical trial, a recommendation of a particular form of treatment, or other recommendation.

Such a model may be a learning model in that information is being added to the system in real time, and the recommendations made by the system may also change over time. For instance, information may be added, deprecated, deleted, or updated, such as adding information relating to patients, studies, journal articles or other information. Additional information may be added as tuples to the graph-based data model. The inference engine may use such additional information to make one or more inferences regarding the data model.

Figure 2:
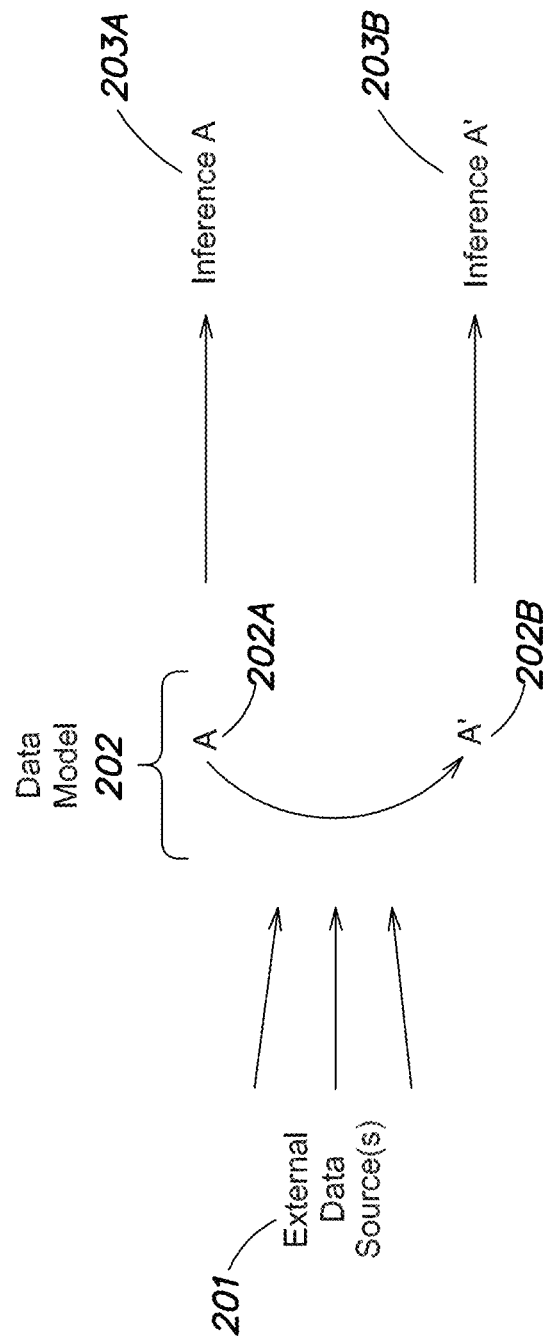
FIG. 2 is a diagram of a process for determining actionable inferences according to one embodiment of the present invention.

FIG. 2 shows a diagram whereby one or more external data sources 201 provide data to a data model 202 (e.g., a data model A (element 202A) at a particular point in time). At a first point in time, the data model A when analyzed by the inference engine (e.g., inference engine 103) yields an inference A (element 203A). After the data model A is updated by one or more data sources, at some later point in time, the data model is transformed to a state A' (element 202B). At this later time, the inference engine may yield an inference A' based on the updated model. Because, according to one embodiment, a graph-based data model may be used, information may be readily added, deleted, or updated over time.

Figure 3:
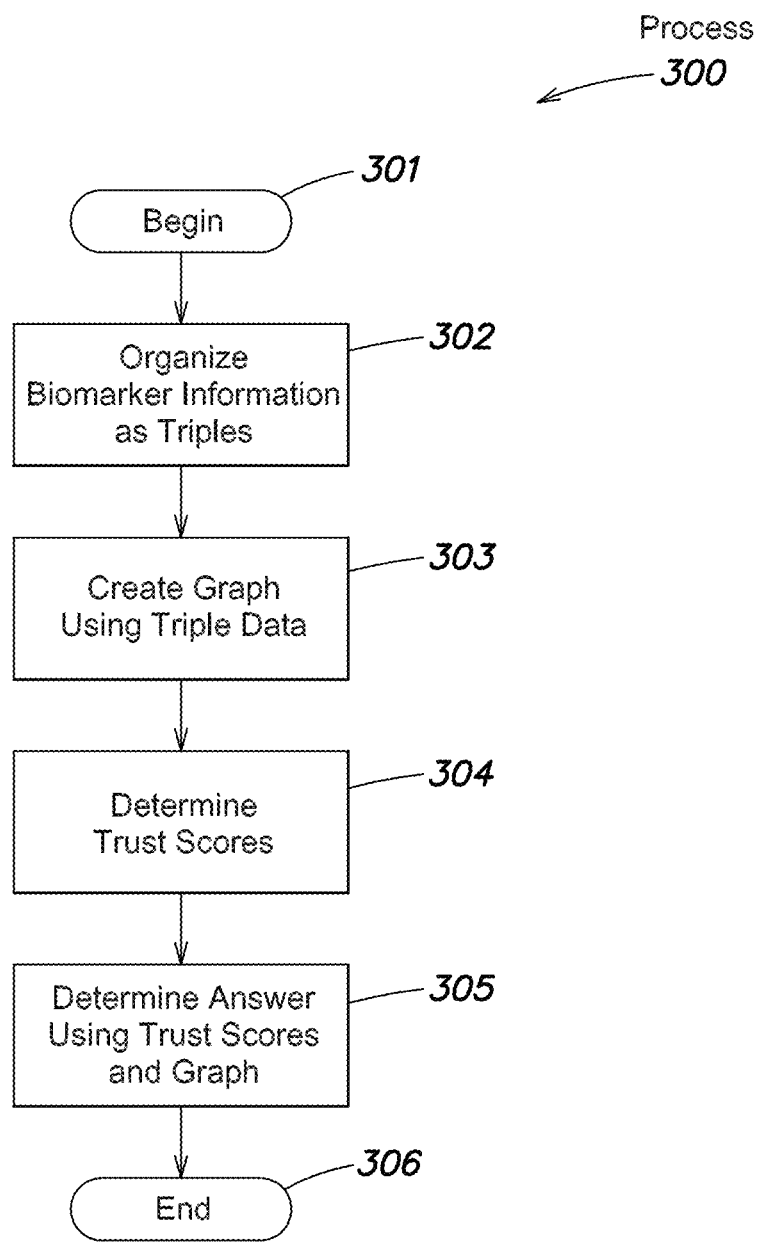
FIG. 3 is a diagram of a process for analyzing biomarker information using a graph-based data structure according to one embodiment of the present invention.

FIG. 3 shows a process 300 for processing genomic information according to one embodiment of the present invention. At block 301, process 300 begins. At block 302, the system organizes biomarker information as triples or tuples as discussed above. Such information may relate generally to gene states, alterations, or other related information, or the information may relate to specific patients (e.g., for the purpose of determining an actionable item with respect to a particular patient). At block 303, the system creates a graph using triple data. As discussed above, triple data may be combined to form a walkable graph that allows a determination of an actionable item. The triples may be organized in treelike data structures that lead to leaves which are the actionable items.

A block 304, trust scores may be determined for one or more relations within the graph model. As discussed, trust scores may be used to determine the likelihood that a particular actionable item will be recommended or followed. At block 305, the system determines an answer using the trust scores and graph model. For instance, the system may provide one or more recommendations to a user in the form of an actionable item that should be followed based on the graph and trust scores. A block 306, process 300 ends.

Figure 4:
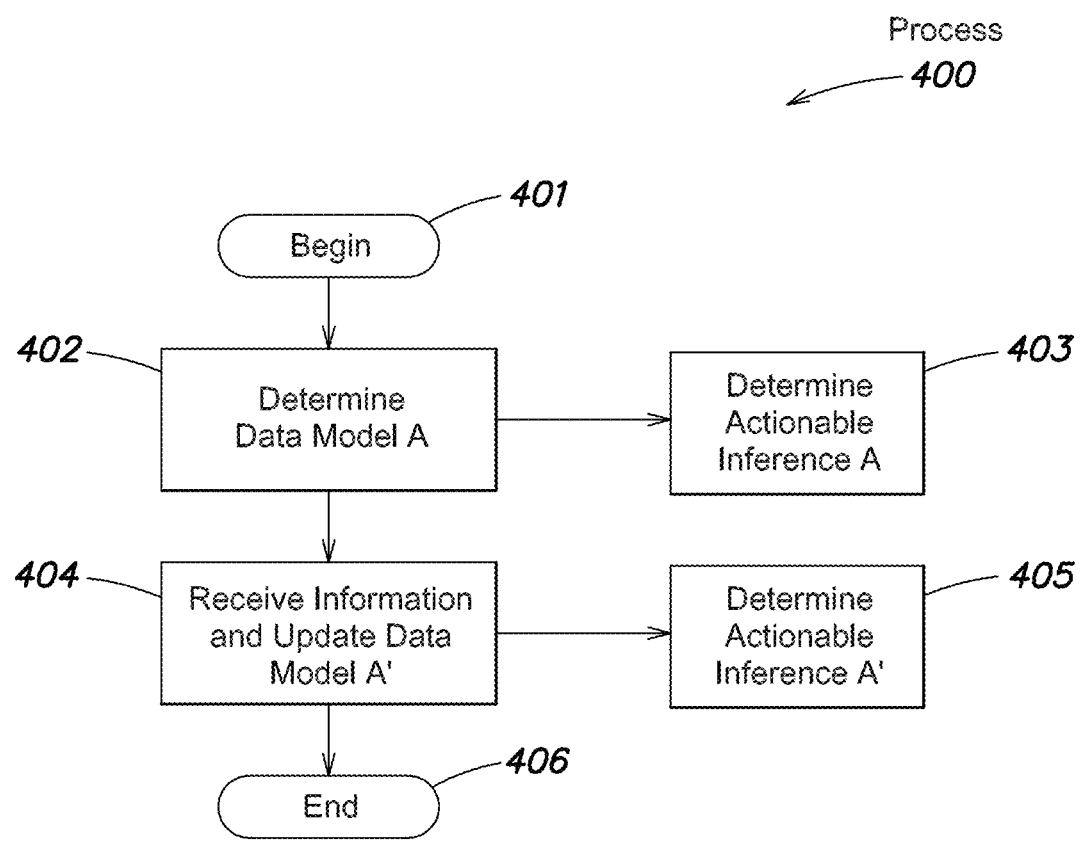
FIG. 4 is a diagram of a process for determining actionable inferences according to one embodiment of the present invention.

FIG. 4 shows a process 404 determining actionable inferences and/or clinically relevant information according to one embodiment of the present invention. At block 401, process 400 begins. At block 402, a computer system may determine a data model A which represents a data graph model determined at a particular point in time. As discussed above, and inference engine may determine an actionable inference A at block 403 based on the determined data model A. At some point later than the previous point in time (e.g., at block 404), the system may receive one or more portions of information and may update data model A to a different state A'. At block 405, and inference engine may determine an actionable inference A' based on the updated data model state A'. At block 406, process 400 ends. Notably the data model (e.g., model A in the example) may be updated in real time, and actionable inferences (or clinically relevant information) may be determined in real time as the model changes. In most conventional systems, they are inflexible to changes and therefore are not conducive to the acquisition of real-time information. Further, in the cases where systems have rigid relational constructs, such systems do not easily handle updated information.

Figure 5:
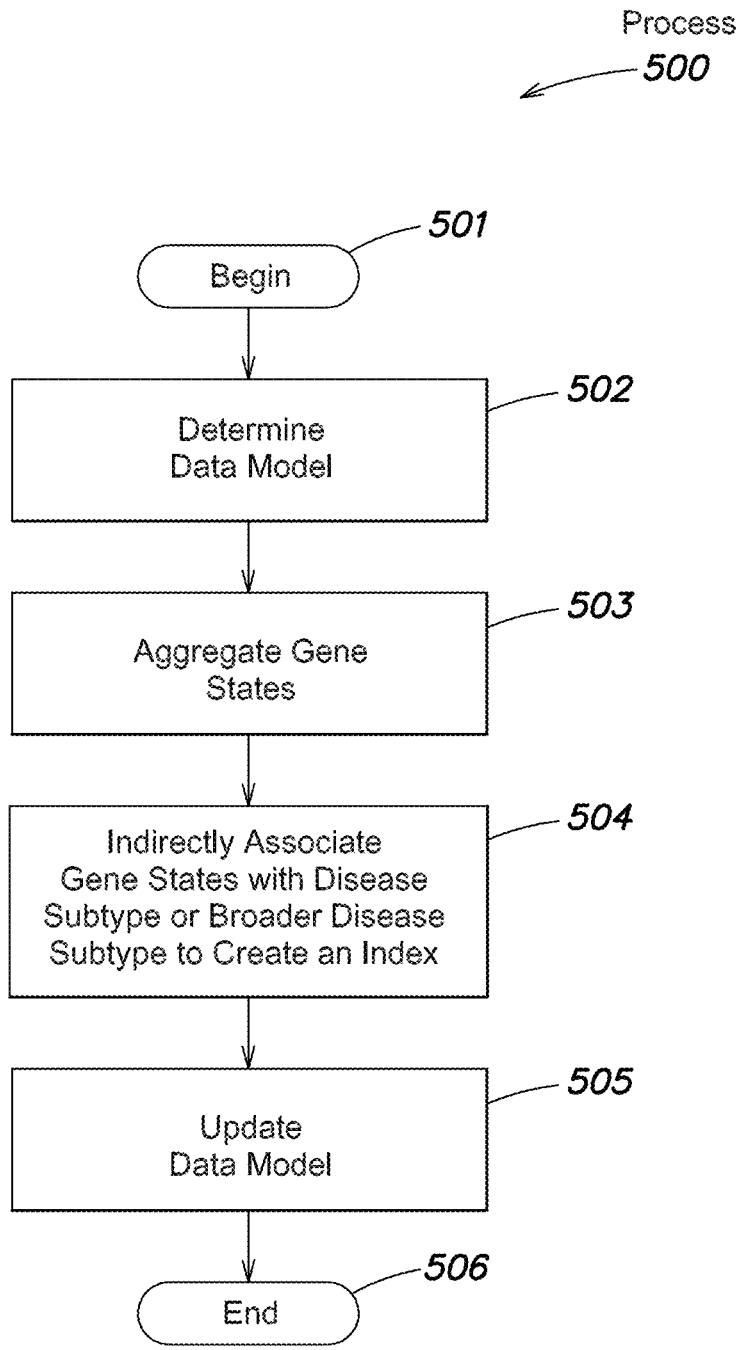
FIG. 5 is a diagram of a process for creating and accessing a data model according to one embodiment of the present invention.

FIG. 5 shows a process 500 for determining a data model according to one embodiment of the present invention. At block 501, process 500 begins. At block 502, the system determines a data model (e.g., a graph-based data model as discussed above). At block 503, the system aggregates gene states into groups. For instance, gene states may belong to an alteration group which is a combination of criteria are attributes, usually clinically relevant, that make the set of gene states within it unique. At block 504, the system indirectly associates gene states with disease subtype or a broader disease subtype to create an index. According to one embodiment of the present invention, is appreciated that a disease alteration group association, referred to hereinafter as a capital DAGA element may be used to aggregate, into a knowledge element, relationships between a disease in an alteration group. Further, the DAGA element associates the coupled index with actionable elements (e.g., therapies, clinical trials, and interpretation of the alteration in the context of the disease). According to one embodiment, the DAGA provides aim main index for discovery of actionable items for patient, such as therapies or clinical trials.

At block 505, the system receives information that is used to update the data model in real time. At block 506, process 500 ends.

Example

Graph Representation

Figures 6A, 6B:
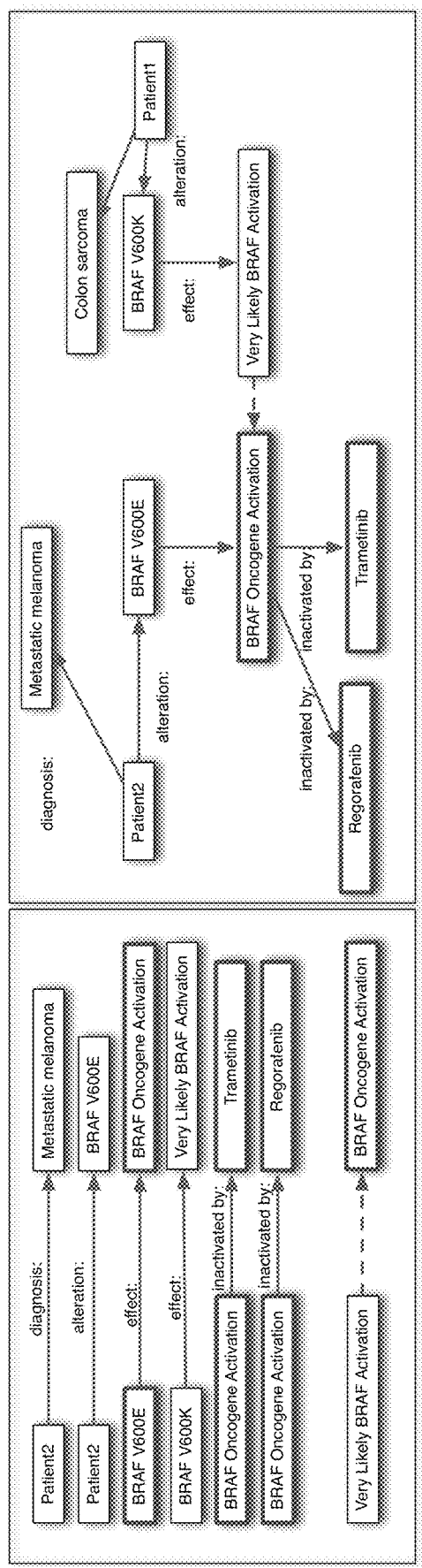
FIG. 6A shows an example data set of tuple or triple information according to one embodiment of the present invention.
FIG. 6B shows an example walkable graph created using the example data set of FIG. 6A.

As discussed, according to one embodiment, graph modeling may be used for data modeling and representation. Graph models differ from relational models in two aspects: 1) they make the relation between data elements explicit, that is, each relationship has a name or an identifier; 2) they represent information as a list of triples or connections. This type of data representation allows for highly flexible data representation and exploration, as well as propagation of information. Consider the example representation using a graph model is depicted in FIGS. 6A-6B, as a list of triples in the left (FIG. 6A) and as an assembled, walk-able graph on the right (FIG. 6B). Notice that in the example graph model shown, every relation (green arrows) is explicitly stated as a triple rather than needing to implicitly state such relations as in the relational model. This requirement enables unlimited pieces of information to be stored about a given element (e.g. Patient 1 is a smoker), even if the same type of information does not exist for other elements of the same kind. In other words, the graph model allows extreme sparseness.

Further, such a structure allows the easy addition or removal of connections such as the one depicted in red (inference): if a physician is faced with an alteration in a patient (e.g. V600K in Patient 2) that is very likely to have a similar effect to a known alteration (V600E), the red connections can be activated, which will allow an algorithm walking this graph for data discovery, to follow the extra link to discover the same therapies. If, instead, the physician has enough information about the patient's alteration, the red connections, or inference, can be turned off. The information in FIG. 6A is represented as a list of triples, and the information shown in FIG. 6B is the same set of triple information organized as a walkable graph.

Figure 7:
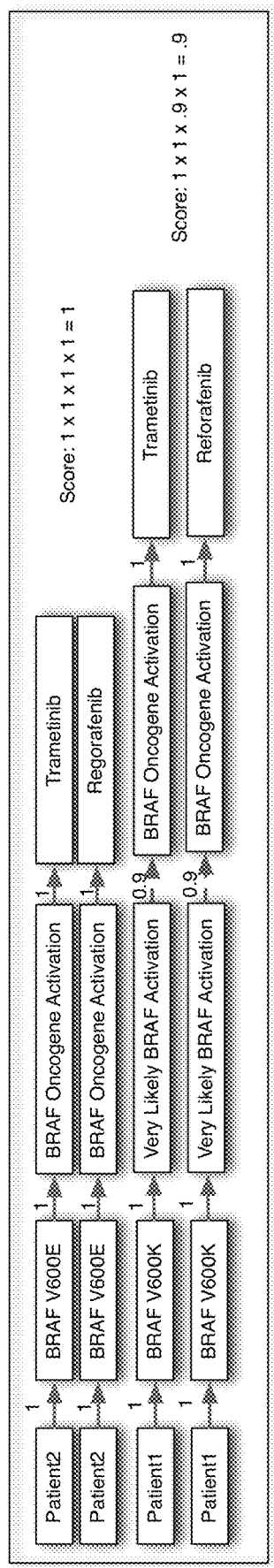
FIG. 7 shows an example usage of trust scores according to one embodiment of the present invention.

It is worth pointing out that the inferred state and the non-inferred state, are not equivalent according to one implementation. The inferred state, in one embodiment, always includes a weight associated with the red arrows that were followed in the path—based on subjective observation or the accumulation of evidence derived from the certainty that a physician has in the inference (red) connections. This example shows another characteristic of graph data models: the relationship itself need not be a simple description— these models allow the assignment of a score to each relation reflecting the trust in each link. In one embodiment, the final trust in the answer can be computed by multiplying the scores of each path or connection followed to derive an answer: As shown in FIG. 7, results of the graph walk mechanism is shown, including an with inference. In the example shown, trust cores are calculated by multiplying the weight of each path relation.

One particular type of graph-based model that may be used is the resource description framework model (RDF). RDF was devised as part of the linked data effort and it emphasizes usage of universal identifiers where available. For example, if Trametinib had been previously described in other systems, the identifier may be reused as opposed to creating one de novo. In another implementation, a universal identifier can also be dereferenceable. That is, it should be possible for anyone wishing to reuse an identifier, to learn more about what that identifier identifies before they decide to use the identifier. RDF leverages the architecture of the web for that: universal identifiers in RDF have the shape of a universal resource locator (URL) such as http://dbpedia.org/data/Trametinib.n3. Typically, more information about what is identified by that URL can be discovered by following that link.

The use of global identifiers greatly increases the amount of information that can be made accessible to the data discovery algorithm: upon hitting such a URI, the algorithm could simply follow its link (dereference it) and retrieve the associated triples (e.g., the information that the molecular weight of Trametnib is 615.39). This simple added functionality has a multiplier effect: when universal identifiers are used, it becomes possible to make use of information that is distributed on the web instead of relying only on information that is available locally, potentially enabling the use of the World Wide Web as if it was a local database. Issues of trust in the source of data can be resolved with the operation described in FIG. 7 (e.g. certain sources of information or certain tuples may have more or less trust in their assertions). In one implementation, information represented in RDF can be queried and managed using SPARQL—a standardized query language devised specifically for RDF.

To exploit the granular data elements necessary for a precision medicine representation model, consider a case in oncology where a physician is looking for information on whether a set of biomarkers for a given patient will affect treatment decisions, i.e. whether these biomarkers, combined with the patient's specific pathology, provide information on the patient's susceptibility or resistance to a particular set of therapies or whether the patient is eligible to enroll a clinical trial. For the purposes of the model, actionability may be defined as the potential to reach one or more leaf nodes as the results of walking a decision graph. Leaf nodes, in one implementation, may either be therapies or clinical trials (e.g., actionable items). In another example implementation, tree branch decisions are based on context items (e.g., disease or gene alteration). Actionability items (e.g., therapies, clinical trials) are therefore, in one example implementation, a function of context items (disease and gene state):

{therapies,clinical trials}=$f$(disease,{gene state})

According to one aspect of the present invention, the representation model may be developed with the goal that some sort of message or report is provided to the physician, and the system using such a model delivers information on actionable items given a context. For instance, according to one embodiment, the representation may be in the form of a user interface provided by a computer system.

According to one embodiment, a number of elements may be combined to compose the representation of the model. Such granular elements may include the following:

Disease (Context Item): The specific pathology that the patient has been diagnosed with. A disease may also refer to a higher-level pathology group (e.g. breast cancer), which itself constitutes an aggregate of pathologies.

Gene (Context Item): A biological entity relevant for a precision medicine decision. For the purposes of the model described, a gene can be treated as an operator with state, affecting one or more dynamic processes in the cell. A "normal" gene state, i.e., the state or combination of states that may be found in a "normal" or "non-diseased" cell can be referred to as its "wild type" state. Multiple genes may affect a single actionability/therapy decision.

Alteration/Biomarker (Context Item): Any gene in the human genome may be altered from its wild type or normal state. When genes are prevalent and predictive of response to therapy or tumor aggressiveness, they are called biomarkers. As used herein, biomarkers correspond to specific "gene states" that are relevant for a precision medicine decision— gene states may include the gene in its "wild type" form. For each gene, there are thousands of possible gene states: from the most extreme to the least extreme, gene states may include changes in the number of copies of the gene (amplifications, losses, deletions); removal of part of a gene (splices, truncations, rearrangements) or point mutations in the sequence that cause alterations in the resulting protein (missense, nonsense). A gene state may also include methylation at various positions in its sequence.

Therapies (Actionability Item): There may be multiple therapies (T) as the output of the graph-walk shown in FIG. 6B and they are associated with one or more genes. In one embodiment, therapies are part of an actionability decision and not the context. As described above, it is the association between genes and therapies that fundamentally changes the paradigm of knowledge organization from more traditional health IT environments. Because, according to one embodiment, different genes may be linked with the same therapy, the total T relevant for an actionability is not the sum of the therapies of the genes (T|G) but rather the number of distinct therapies for all genes: distinct(T|G).

Clinical Trials (Actionability Item): There may be any number of CTs and they may be also associated with genes.

References (Actionability Provenance Item): The number of references in the report is the distinct combination of references justifying decisions on therapy and clinical trial choices.

Complex Data Elements

Complex data elements may be used as knowledge hubs, i.e., a combination of one or more of the basic representation elements described above. They may be designed to store individual pieces of information that are derived from a combination of two or more basic elements (e.g., an FDA approval status for a therapy/disease combination).

A text node element may be used to store, in the hierarchy, information relevant for rendering decisions in a precision medicine system. For example, a text node element (FIG. 8, box 1) stores a piece of content, and connects the content to three dates: a modified date, a reviewed date and a retired date (if the text has been retired). The text node element stores information about individual elements (e.g., genes, alteration groups, diseases, therapies), that are relevant for precision medicine decision-making. These three dates are part of the knowledge deprecation mechanism that, according to one implementation, includes a set of rules that defines how the content of the text nodes is updated. The deprecation mechanism allows for two types of changes: either the content was just syntactically modified (e.g. a comma was added) or the content was reviewed in the context of a new piece of information (e.g. when a new relevant paper is published). Text nodes may contain links to citations or to other entities mentioned on the content (e.g. other genes, pathways, etc.). It should be appreciated, however, that other deprecation mechanisms may be used.

Disease Hierarchy

As discussed above, a disease and a set of gene alterations may be used to provide the primary elements for discovery of actionability for any given patient. To maintain consistency of knowledge content, in one implementation, it may be required that the disease is a term extracted from a controlled vocabulary. This controlled term may be managed as part of a hierarchy of disease terms, where each branch from a root node all the way to the leaf nodes is characterized by narrowing of the child nodes in relation to the parent nodes. This hierarchy provides a convenient means of describing a phenotype in increasing details. A fully comprehensive disease hierarchy may extend as deep as the genes and alterations driving the phenotype, if these were also known. In practice, other than the single gene-disease associations described in databases, in the majority of cases there is no single gene driving/causing a phenotype, but rather a complex network effect.

Gene Alteration Group (AG)

Figure 8:
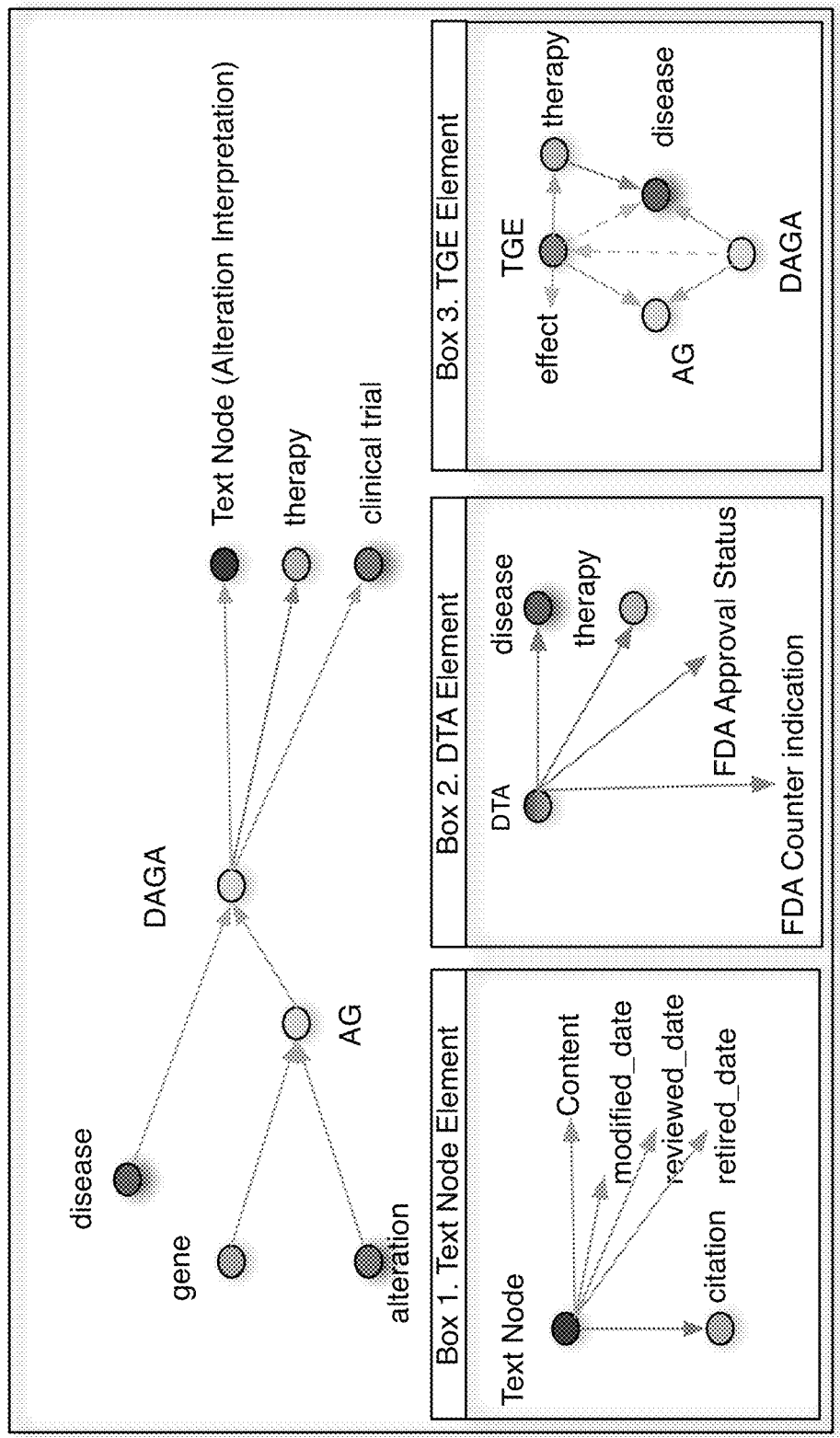
FIG. 8 shows an example DAGA model element, text node element, DTA element and TGE element according to one embodiment of the present invention.

As described further below, a Gene Alteration Group (AG) as defined herein aggregates gene states into groups. In one embodiment, each gene state belongs to a single alteration group. In spite of the many thousand possible gene states, many of them have the same effect in a cell, i.e. the expression of a biological entity expressed by that gene (e.g., a protein, a silencing RNA) has an effect in the network dynamics of the cell. As such, states can be aggregated based on this implicit dimension rather than their descriptive evidence. For example, a tumor suppressor gene may be inactivated (i.e. prevented from carrying out its tumor suppressing function) in a number of different ways, such as truncation of the binding domain, methylation, etc. All those possible states can therefore be aggregated into an alteration group of inactivating alterations. The following set of rules may be used, either alone or in combination, for the creation of gene alteration groups:
(1) Each gene state may be belong to a single alteration group
(2) An alteration group is a combination of criteria or attributes, usually clinically relevant, that make the set of gene states in it unique
(3) There is no limit to the number of criteria that can be included when making an alteration group unique
(4) Individual gene states may fall into its own alteration group—this is the maximum granularity that an alteration group may have Disease Alteration Group Association (DAGA) Element A DAGA element may be defined within the hierarchy as a data aggregator. According to one aspect, it is appreciated that it may be one of the most important knowledge aggregators (FIG. 8, main box). In one implementation, the DAGA element is the knowledge element that represents the relationship between a disease and an AG and associates that coupled index with actionable elements (e.g. therapies, clinical trials and an interpretation of the alteration in the context of the disease):

DAGA=(AG⊥disease)

A more general case of a DAGA is a D(M)AGA (disease multi-alteration group association), where a disease and a set of alteration groups in the same gene are represented together as relevant for actionability.

Disease Therapy Association (DTA)

A disease therapy association (FIG. 8, box 2) may be used to associate a disease and a therapy with any other information that is relevant for this combination. The DTA can be used to capture annotated FDA status (approved/non approved) in specific therapy/disease associations or specific counter-indications.

Therapy Genomic Effect (TGE)

Targeted therapies act upon genes, sometimes on specific states, and may either activate or inactivate genes. The therapy genomic effect node (FIG. 8, box 3) makes it possible to capture the link between the gene targeted by the therapy and its known effect. For example, Lapatinib is a therapy used to treat breast cancer that interrupts the HER2 and the EGFR pathways by inhibiting these two tyrosine kinases. The therapy genomic effect (TGE) is the knowledge element that captures this interaction between a drug and a gene. Many therapies target only a particular state of the gene (a version of the gene with a specific variation from the wild type) and not others. As such, the link between the gene and the therapy must be established through the particular alteration group that the therapy targets. In some cases (e.g. alterations in KRAS codon 12 in colorectal adenocarcinoma), the disease in which the alteration occurs is relevant—in those cases, the TGE element must also include a link to the diseases in which it is relevant.

As mentioned above, FIG. 8 shows one implementation of complex knowledge elements for supporting precision medicine decision making. The DAGA may be defined as a function of a disease and an alteration group. An alteration group, in turn, is a set of alteration in the same gene, which share some property such as their actionability items. The DAGA provides the main index for the discovery to actionability items for a patient, such as therapies or clinical trials. A rationale for that actionability can also be attached to the DAGA, which refers to a specific gene, a specific disease and the reason for a given set of therapies or clinical trials.

Core components for the management and propagation of DAGAs are the Text Node (Box 1), which is key for provenance of actionability information; the DTA (Box 2), which associates a therapy and disease with an FDA status or counter indication; and the TGE element (Box 3), which associates a therapy and an alteration group for a given effect (e.g conferring sensitization or resistance) and, in some cases, a disease.

The elements described in the previous section support a set of emergent complex operations, which ultimately support precision medicine decision-making and enable an algorithm to walk the decision tree in FIG. 6B to a reliable decision leaf. Below is described some of those operations.

Knowledge Propagation

One of the key advantages of knowledge representation as a graph is that information can propagate in the graph according to predefined rules. Consider, for example, the DTA: when combined with the disease hierarchy, it allows propagation of the "approved/not-approved" status in the disease ontology tree, from the broader terms to the narrower terms (but not the other way around). Consider disease D1, which is a disease described in the disease hierarchy as being broader than D2 (D1—BroaderThan—D2). If a DTA has been defined for D1 for any given therapy, DTA' for D2 and that same therapy can be calculated as:

DTA'=DTA((broader(disease))⊥therapy)

FIG. 9 shows a knowledge propagation operator defined as a SPARQL Rule. For example, Lapatinib is approved for breast cancer. Because the disease ontology tree described above is a curated hierarchy that describes all diseases that are "narrower" than breast cancer, the DTA can be used to propagate the attribute to all diseases downstream of the root disease "breast cancer" as shown in FIG. 9. Similarly, drug counter-indications can also be propagated in this manner.

Figure 10:
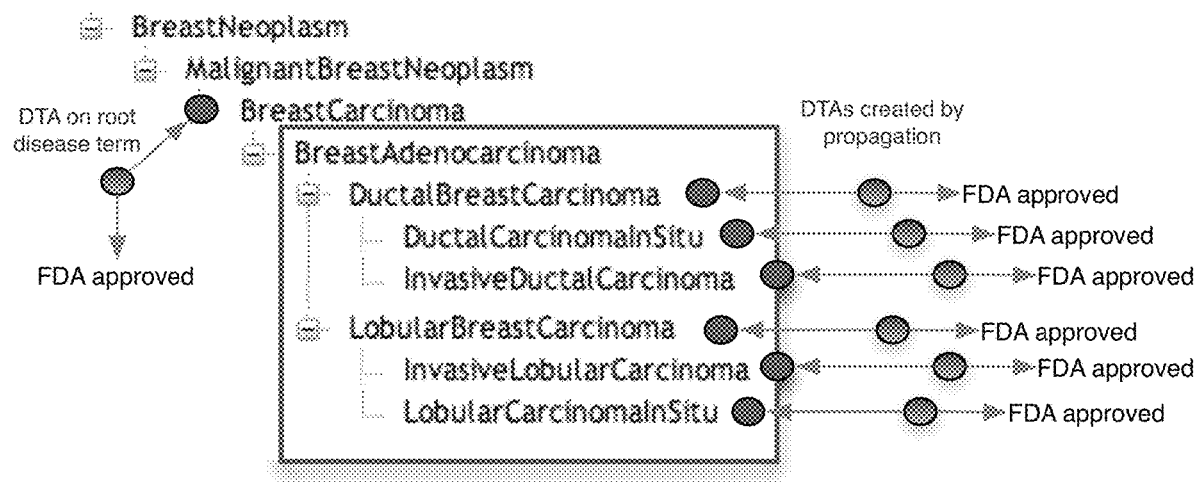
FIG. 10 shows an example of propagation of data according to one embodiment of the present invention.

FIG. 10 shows an example of knowledge propagation in the element hierarchy. For example, knowledge propagation may be enabled by the combination of a complex knowledge element, such as the DTA or the DAGA, and a tree specifying the relationships (broader and narrower) between one of the elements present in the complex node (e.g. disease). An example of knowledge propagation in precision medicine is the ability to infer novel DTA instances by traversing each of the child nodes of the disease ontology tree. In that scenario, and others similar to it, the disease ontology tree can be treated as a set of propagation rules that guide inference of new knowledge. Other types of propagation rules are possible but we have not included those in our model. According to another embodiment, the system may implement a deprecation operator to update text elements. For instance, in one implementation, when information is added to a model from multiple sources, it is appreciated that updating the content of the text elements should be an asynchronous mechanism. That is, messages that arrive later in the system are not necessarily more correct than messages that arrive earlier. A scalable system may be used to prioritize content based on information value. As such, an operator for text content deprecation in one example requires as inputs the content itself, the date when the content was produced, and the date when the content was reviewed.

Figure 11:
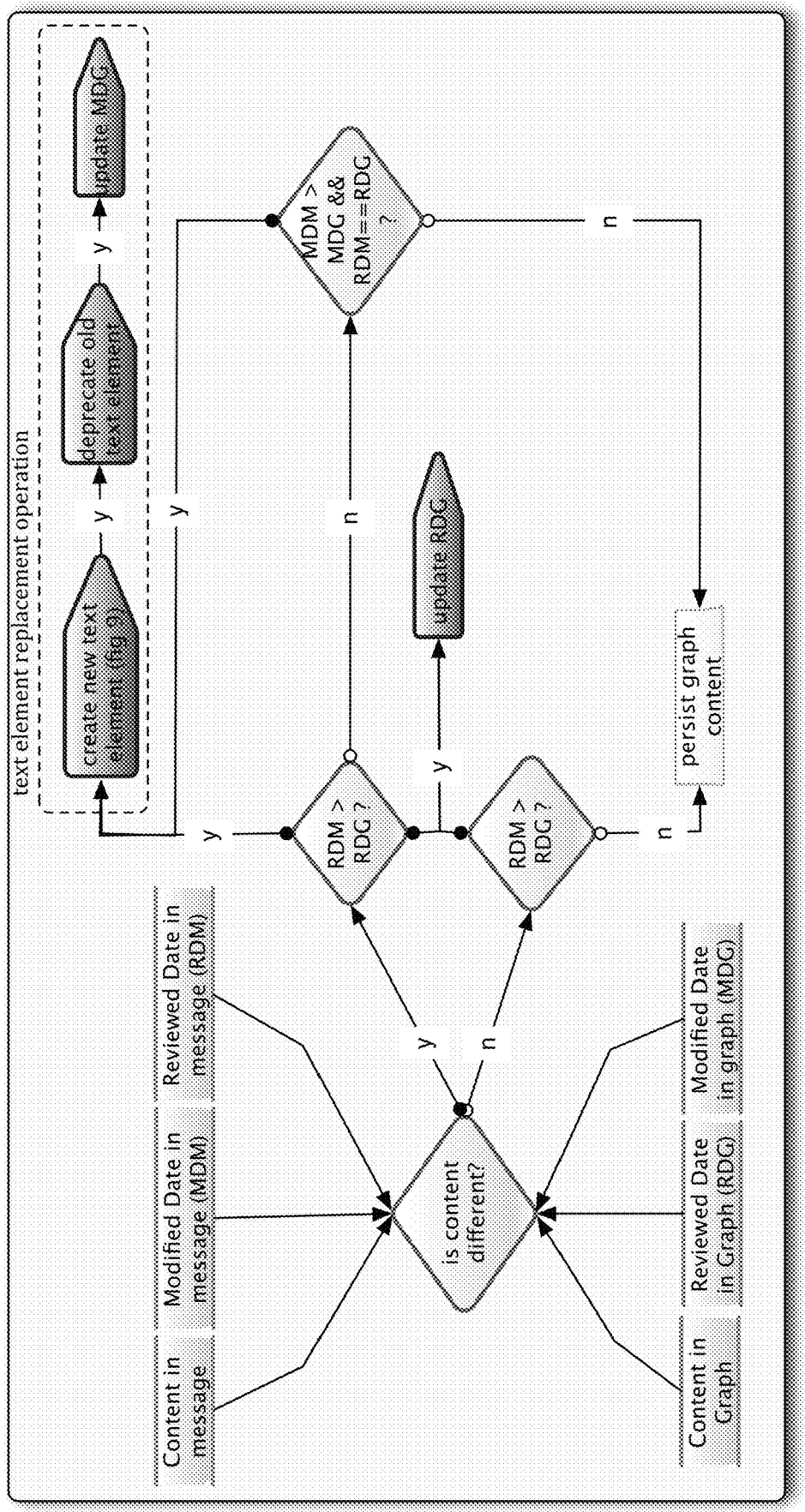
FIG. 11 shows an example process for updating text element information according to one embodiment of the present invention.

According to one embodiment, the functionality of the operator is as follows as shown by way of example in FIG. 11: when a message is received, the content is compared against the existing message in the graph model. If the content is different, reviewed dates in the message and the graph model will be compared. If the reviewed date in the message (RDM) is more recent than the reviewed date on the graph model (RDG), the text element replacement operation is triggered: a new text element is created and the RDG is made to match the RDM; this new text element is linked to the DAGA about which the message pertains; the old text element is "deprecated", i.e., the old element is given a "retired" date and unlinked from the DAGA. If, however, both the RDG and the RDM have the same value but the modified date in the message (MDM) is more recent than the modified date in the graph model (MDG), then the text element replacement operation is still triggered with the exception that the RDG persists.

According to one embodiment, a deprecation operator is provided that allows: 1) asynchronous updates driven by time-points contained in the message; 2) concurrent updates that avoid replacing content with higher information value, i.e. reviewed content is to not be overwritten by modified content, which has less information value; 3) reconstruction of the state of information about the DAGA at any point in time and, subsequently, supporting very targeted reversal of information content.

Also, the system may include an alteration group operator that merges gene states having shared actionability items and which reduces the complexity of the hierarchy. Graph models uniquely allow for the creation of circular relationships or redundancy. For instance, a therapy can be related to a disease, which can relate to a gene, which can be targeted by a therapy. As described, alteration groups may be used to aggregate gene states based on their actionability. Actionability, in turn, can be re-defined from a cellular perspective as the potential to transform the cell state from a cancer state to a normal state through the use of targeted therapies. For the purposes of this simplistic description, consider the normal cell state as one in a set of states in which the cell behaves similarly to its neighbors.

Example Implementation

Figure 12:
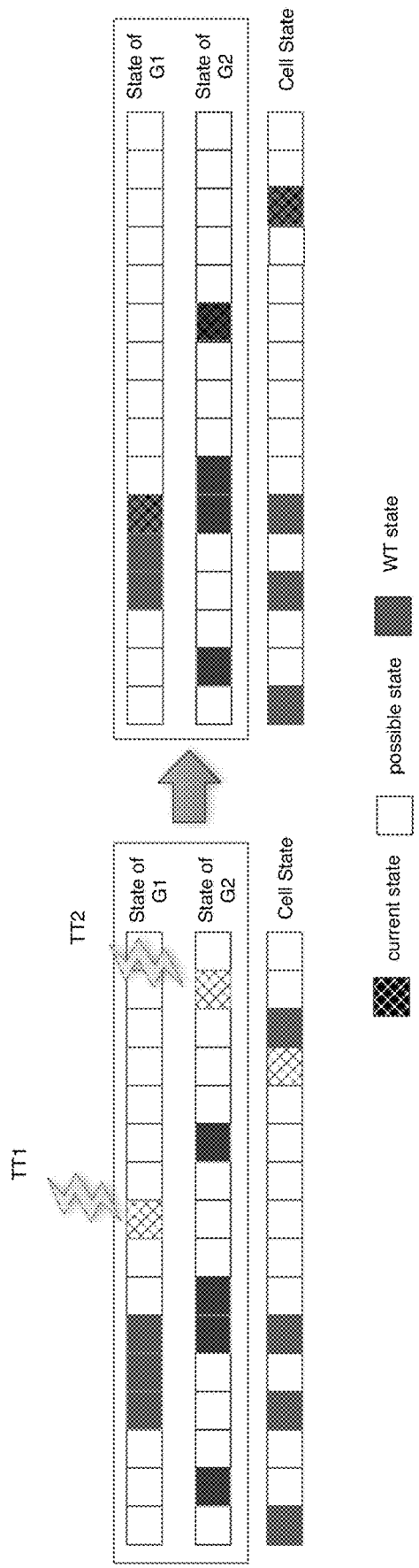
FIG. 12 shows an example gene state that may be modeled by a system according to one embodiment of the present invention.

A corollary of precision medicine is that deviations from a cell normal state are corrected by applying targeted therapies that return gene states from altered to unaltered as shown by way of example in FIG. 12.

As shown in FIG. 12, from all possible states (boxes) in which a gene or cell can be found only a few are wild type states (full boxes). The state of the gene (blue, green boxes) and the state of the cell (red boxes) are intertwined in the sense that the combinations of states for multiple genes affect the state of the cell. Targeted therapies (TT) act as a trigger that turns an altered gene state (hashed boxes) to a normal gene state, which in turn transforms a cancer cell state into a normal cell state.

A single therapy can often return a gene to its normal state from a number of alternative states. As an example, many different states can lead to the activation of an oncogene. A targeted therapy that inactivates the product of that oncogene is therefore the agent of operation for any of those states. As such, a naïve approach to the creation of alteration groups is to aggregate all of those states in a single alteration group. However, because not all cells have the same normal states (e.g. normal for a lung cell is very different from normal for a liver cell), it is often not enough to stop there—the phenotype of the diseased cell type also plays a role. This creates a circular reasoning problem: if actionability is decided based on a disease and an alteration group (DAGA), alteration groups cannot be decided based on actionability of DAGA (since the alteration group must already exist). This would be the case if one assumes a static model where alteration groups "must be right" before DAGAs are created.

Figure 13:
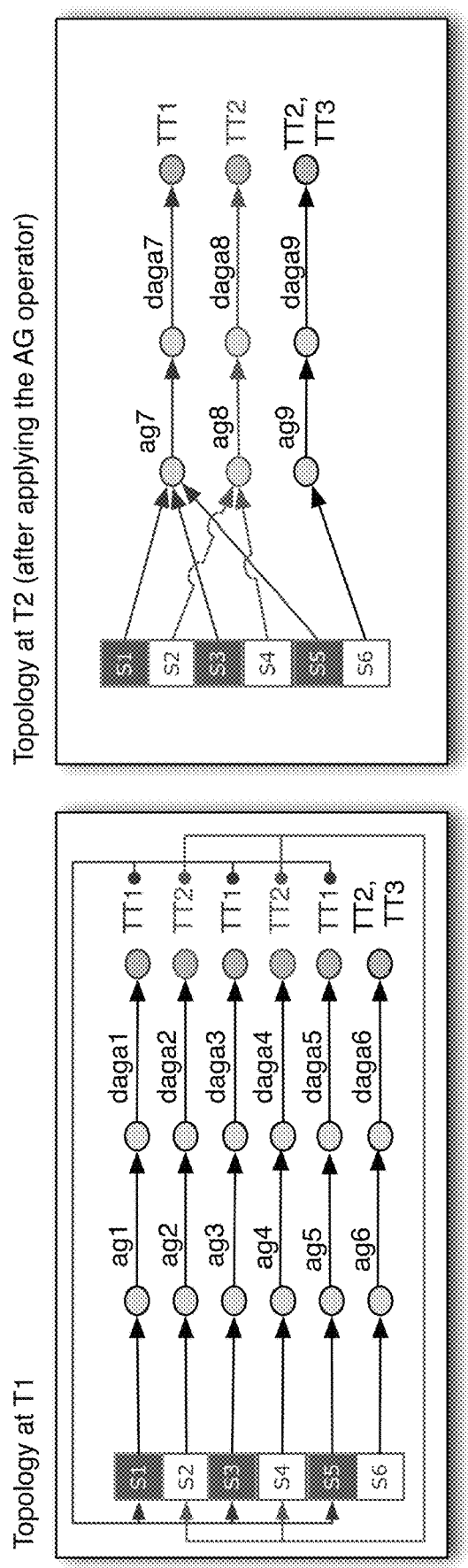
FIG. 13 shows an example application of an AG operator according to one embodiment of the present invention.

However, consider the following model: when a DAGA first gets created where an alteration is associated with a disease, an alteration group may be created particularly for that alteration. As more DAGAs are created and actionable items are added to those DAGA, the same actionability items can appear to be associated with many alterations regardless of the disease. Once a number of such DAGAs exist, it is possible to discover a list of alterations that share the same set of actionable items no matter which disease is used in the search for a DAGA. That circularity of the graph model is what allows alteration groups to be defined dynamically by shared actionability items and the DAGAs can be created again. This circular operator can be run as often as necessary and DAGAs can be added/removed dynamically to always reflect the latest knowledge about sets of alterations and actionable items. As shown in FIG. 13, an alteration group operator may be used to recompute the topology of the graph model, thus significantly reducing its complexity by merging gene states (Sn) where the actionable items (TTn) are the same regardless of the disease.

As discussed above, basic components and operations may be used to assemble a graph model for representation of information relevant for precision medicine. Not unlike traditional medicine, precision medicine decision-making is often an iterative process that follows a path in a decision tree, even if not formally represented in a computer system. The difference between the two is that a precision medicine decision tree, due to the need to include up to 30K genes and alternative states for each, is many times larger and will likely continue to grow as more knowledge is acquired about the molecular causes of disease.

In practice, the large majority of possible diseases x gene state associations (DAGAs) do not have any actionable items associated, i.e. there are no therapies or clinical trials relevant for the association, which makes the disease x gene state matrix extremely sparse. As such, a model that stores only associations that do exist has immediate benefits over a model that imposes a rigid schema. Moreover, the association between the disease x gene state association and a given therapy is also not always the same, i.e. a given gene state may make the patient susceptible or resistant to a therapy. As such, traditional information representation methods that rely on implicit rather than explicit relations impose unnecessary constrains on the ability to represent novel relationships and to expand the model as new ones are discovered. Instead, in one graph model representation, associations are created between fundamental elements (e.g., genes, diseases, therapies) through knowledge hubs that enable, through the definition of a simple set of rules, information to be inferred as described in the knowledge propagation operator. Information represented with graphs models (e.g., RDF) can be traversed and discovered using fast algorithms that have been optimized to work with petabytes of information on the web. Furthermore, since there are no constrains imposed by a rigid schema, knowledge can grow and old assertions be deprecated (e.g., using a deprecation operator) without the need to detach them from the knowledge hubs that they refer to.

Further, it is appreciated that data compression is enable by the AG operator. For example, in the analysis below, effects of the operators described with data collected from a total of 8758 individual medical cases, in which there were a total of 10699 distinct gene states in a total of 301 genes (Table I below). Each of these gene states was associated with one or more disease subtypes through the creation of a DAGA. A total of 440 disease subtypes were used in the model. Overall, the distribution of gene states across various cancer subtypes were found to be homogeneous. An assumption may be made that any gene state may occur in any disease subtype. In the example, a total of 34918 DAGAs were created from a space of 4 707 560 possible associations (i.e. 0.7% of possible gene state/disease subtype associations have been observed).

TABLE I

Number of cases analyzed and specific gene state/disease associations discovered

| Number of Medical Cases | Number of Genes | Number of Gene States | Number of Diseases | Number of DAGA Elements |
|---|---|---|---|---|
| 8758 | 301 | 10699 | 440 | 34918 (0.07% content) |

As discussed, according to one embodiment, the DAGA may be used as the index associating gene states with disease subtypes. It is appreciated that the DAGA, in the example implementation, is the knowledge hub that grows the fastest and is likely to continue to grow even faster as new methods improve the ability to distinguish between disease subtypes and gene states. Is it therefore expectable that over time the number of DAGAs ($N_{daga}$) will grow at a rate of O(disease subtypes x gene state), quickly making the problem of decision making in precision medicine an intractable problem, i.e. a problem that cannot be addressed with current computers. For that reason, it is critical to identify features that enable compressing these potentially exploding numbers into computable operations. Given that the problem that the example model attempts to address is that of traversing the graph to find actionable items (therapies and clinical trials), a compression solution may be used that applies known actionability information to evolve the topology of the model using the cyclic property of graph models (AG operator).

Figures 14A, 14B:
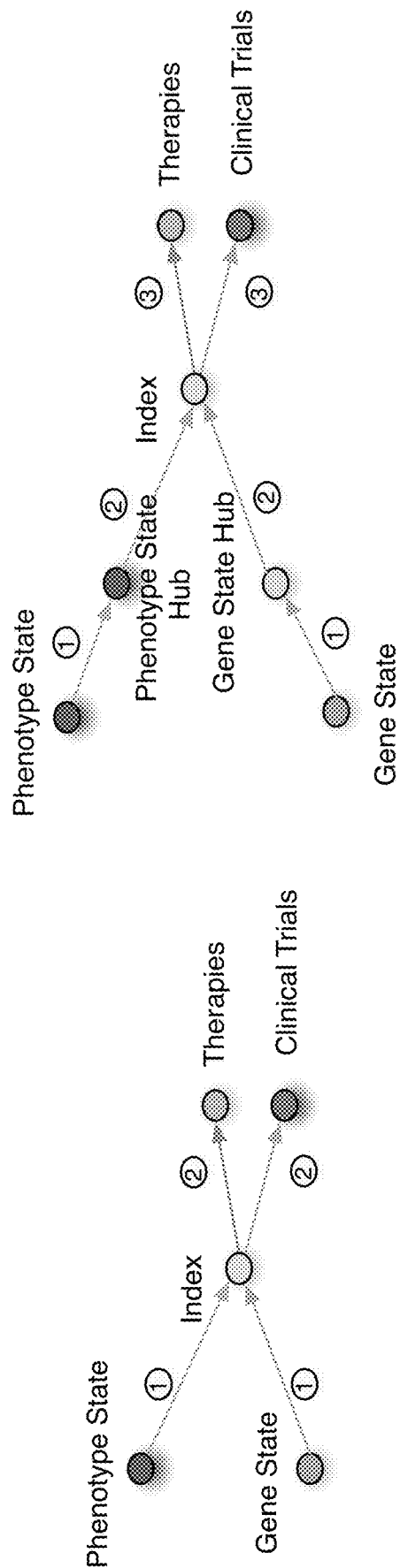
FIG. 14A shows a direct association of gene state and index.
FIG. 14B shows an indirect association of gene state and index according to one embodiment of the present invention.

FIGS. 14A and 14B show two methods of structuring the index connecting context items with actionable items: a naïve method (FIG. 14A) associates a disease subtype with a gene state directly. The DAGA method associates a disease subtype (or a broader disease subtype) with an alteration group. The index supporting the discovery of actionable items given context items can be structured in two possible ways: either the index is created as a combination of the disease subtype and the gene state (naïve approach) or, as in the case of the approach described above (DAGA approach, FIG. 14B), gene states are indirectly associated with disease subtypes by first aggregating them into groups, which are combined with the disease subtype (or a broader disease subtype) to create the index.

In the naïve approach of FIG. 14A, querying the direct association graph requires one less join than in the DAGA approach where states are aggregated into hubs—to recover the therapies and clinical trials in the DAGA approach as shown in FIG. 14B, the system is apparently less efficient in queries—it must first discover the broader disease subtype and gene state group before the query can be completed. Nevertheless, when one considers the sparseness of the search space, the DAGA approach renders useful results with a much higher probability than the naïve approach. Consider the following: given the number of existing gene states (10699) and phenotype states (440) combinations in the system, the search space $N_{daga}$ has size $10699*440=4.7*10^6$.

However, the matrix (M) intersecting the gene and phenotype state is extremely sparse (only 0.07% of the cells are filled). Due to the heterogeneity of this data, the sparseness of the state matrix (M) is extremely high—of all the possible context item combinations, i.e. only 0.07% of the combinations have queriable content and therefore the direct association case would only render content to the query in 0.07% of cases, leaving 99.93% of queries with no results.

Now consider the case where certain gene states and certain disease subtypes could be considered equivalent from an actionability perspective, allowing the creation of hubs or groups. This would result in certain rows (gene states) in state matrix M to be aggregated and certain columns (disease subtypes) to be aggregated, resulting in a state matrix with much less sparseness (M1), where the probability of discovering actionable content in the available query space would be much higher. When one analyses the combination of therapies for each gene states, there is a large number of gene states that render the same therapies. Biologically, multiple gene states have been observed to have the same effect in the overall effect function of a gene (e.g. activation) and therefore can be targeted with the same therapy. Regardless, gene state hubs can therefore be dynamically generated by relying on the following back-chaining rule:

If$((\{T\},\{CT\}|GS1))==(\{T\},\{CT\}|GS2))=>\{GS1, GS2\} \subset GSH1$

Where $\{T\}$ and $\{CT\}$ correspond, respectively, to the set of therapies and clinical trials curated for a particular gene state (GS), and GSH1 is the Gene State Hub aggregating all gene states with the same set of T and CT. When this analysis is run, i.e. creation of gene state hubs by aggregation of gene states based on curated therapies+clinical trial availability, a total of 530 Gene state hubs is found. With this, the dimensions of the new M1 state matrix become $530*440=2.3*10^5$, reducing the search space by a factor of 10. It is worth noting that in this gene state compression exercise nothing is lost since the repeated T and CT are the seed for the compression. Applying the propagation operator further reduces the sparseness of M1 by a factor of X.

Knowledge Integrity may be ensured in the model through redundancy and cardinality rules. The knowledge hubs described above enable knowledge propagation and asynchronous updates given a stream of disease/alteration/actionability association content. The knowledge hubs are constraints in the possible graph associations and that is what makes them useful, e.g., according to one implementation, a DAGA should have only one disease and each alteration should belong to a single alteration group. These cardinality rules are respected by the operators described. It would be useful, however, to allow for more than one method of creating DAGAs or Alteration Groups, particularly when high quality information can be collected from a variety of sources.

As an example, it would be desirable to allow for DAGA actionability associations to be derived from the literature or from public and curated knowledgebases such as PharmGKB. However, these other sets do not necessarily respect the cardinality rules for the operators described and necessary for the discovery of relevant, high quality, actionability information. To enforce cardinality in light of external data injection, cardinality rules may be defined as SPARQL patterns. As an example, each DAGA should have only one disease; before accepting the creation of new DAGAs derived from external sources, data injection may be scanned for its cardinality by applying a SPARQL query to the converted information. For example, the listing shown below is a SPARQL query that looks for instances of DAGAs with more than one disease. If this query returns an empty set, the test passes. This is the same set of cardinality rules that is applied to check overall consistency of the graph model as a whole. If there are problems in the implementation of any of the operators, the SPARQL cardinality rules can be used to detect it.

```
select ?daga where {
    {select ?daga (count(distinct ?disease) as ?dis_count) where
        { ?daga a daga: ; daga_dis: ?disease . }
        GROUP BY ?daga
    }
    FILTER (?dis_count > 1)
}
```

More complex rule patterns may take advantage of redundancy of graph data representation for consistency checking. The following types of example rules may be defined:

Volume: These rules compare the state of the graph with the previous state by counting elements with a given pattern (e.g. number of DAGAs). It is assumed that the number should always increase One to one (1:1): These are the simplest set of cardinality rules—if a knowledge hub (e.g. a DAGA) points to more than one element of a given type (e.g. disease), the test will fail, otherwise it will pass Same Count: These cardinality rules compare the count of two distinct relationships in the graph, not necessarily between two immediately connected nodes. For example, the number of DTA connected to a disease should always match the number of therapies connected to that same disease.

Dangling entities: In graph representational models, "types" can be made explicit (as opposed to relational models, where the type is implied by the table where the information is stored). Specifying that a given node in a graph is of type "disease" or of type "gene" is critical for consistency. As such, these rules check that every element that is used as part of a relation is described to have a "type"

Symmetric relationships: These rules check bidirectional relations, i.e. for every symmetric relationships, such as "DAGA-hasDisease-Disease", the same but opposite relation should also exist "Disease-forDAGA-DAGA"

One to N to One (1:N:1): Some relationships are of type 1:1 rely on propagation of information through some intermediate node. For example, a gene may have relationships to multiple elements of type TGE, one for each therapy that the gene interact with. However, each of these TGE should link to the same Gene.

N to One to N (N:1:N): these rules are the precise opposite of the 1:N:1 rules—e.g. if 5 DAGAs point to the same gene, it is expectable that 5 alteration groups connect to that gene, thus forcing the cardinality (5:1:5)

From an engineering standpoint, the challenges of building a system geared at storing and recalling precision medicine related knowledge stems from 4 major requirements inherent to this domain: 1) that information for medical reporting is kept, as much as possible, in sync with the latest discoveries published in the literature; 2) that knowledge associated with gene alteration effects in disease and treatment can be recalled independently of the context in which they were first discovered; 3) that new gene/gene or gene/disease associations can be easily created and recalled without significant alterations to the data model; 4) that simple/unambiguous gene alteration/drug or gene alteration/clinical trial associations can be inferred for novel alterations (i.e., alterations that have not been reported before), provided that the alteration effects and location are known.

In one aspect, a goal that may be achieved by a graph model includes organizing precision medicine relevant knowledge in a way that it allows the retrieval of the appropriate actionability content (therapies and clinical trials) given contextual items (a disease subtype and a group of gene states). This approach creates an index (the DAGA) that associates actionable content with Alteration Groups (AG) instead of gene states. The rationale text contained in each report is therefore associated with these DAGAs. Other knowledge hubs were presented which facilitate the representation and retrieval of more granular content: the DTA (disease therapy association) element associates a disease with a therapy and an FDA status (for the disease subtype); the TGE element (therapy genomic effect) associates an alteration group, a therapy and the effect on the patient (resistance/sensitizing). In one example shown, a compression of data using the DAGA index using a set of 8758 medical cases obtains a 10× compression of the data.

Example Implementations

As described above, genomic testing provides unique opportunities to make more informed treatment decisions, especially in the field of cancer diagnosis and therapy development. Some conventional approaches can fail to provide useable information within the volumes of information provided as results of genomic testing. Further, it is appreciated that some conventional approaches fail to focus practitioners on actionable information within the genomic testing information and any associated treatment information.

Accordingly, provided are systems and methods for managing genomic testing information that provide a single reporting source for accessing and applying available information on a patient's cancer. According to some embodiments, genomic testing on the patient's cancer provides specific information on the tumor, one or more genes implicated by the tumor, and one or more alterations within the genes. The testing information on tumor, gene, and alteration can be used by the system to manage delivery of curated information that focuses users (e.g., physicians) on actionable information within the genomic test results and associated information. For example, publically available data (e.g., therapy data, clinical trial data, and journal publications) can be interpreted to provide the curated information based on its relationship to one or more of the tumor, gene, and alteration for a patient. The publically available information can be processed on the system to provide navigable data structures informing the user of available actionable information associated with a patient's cancer.

According to one embodiment, by providing users an indicator of actionable information, information within genomic testing reports can be provided succinctly and enable the users to select the indicator to access more detailed information as needed. Further, genomic test results (e.g., listings of alterations) can be ordered based on the presence or absence of actionable information items. In one example, actionability of the navigable data structures can be defined on available information for an FDA approved agent in the patient's tumor type, available information for an FDA approved agent in another tumor type, and/or available information for a mechanistically driven or biologically relevant clinical trial based on the alteration(s) found.

The ordering can be configured to focus the user on the actionable information to facilitate review of a plurality of alterations and their associated information. Indicators of actionable items can be displayed based on an information source (e.g., a therapy indicator/tag references available therapy information items related to a genomic alteration, a trial tag references available clinical trial information items, and a reference tag for reference information items). The indicator can be associated with a respective alteration in the plurality of alterations resulting from genomic testing.

In some embodiments, the system facilitates successive selection of alterations and associated information within the plurality of alteration results, for example, using the indicators. By enabling successive selections, the system facilitates better understanding of a patient's cancer and enables more informed treatment decisions.

According to some embodiments, the actionable information includes identification of FDA approved therapies for a tumor, gene, and alteration combination. Actionable information can also include identification of related therapies that are implicated by any one or more of the tumor, gene, and alteration characteristic of a patient's cancer. According to some embodiments, related therapies can be determined by the system and displayed to users to facilitate treatment decisions. For example, indicators regarding the related therapies can be displayed as part of the navigable data structures within user interface displays generated by the system.

Figure 15:
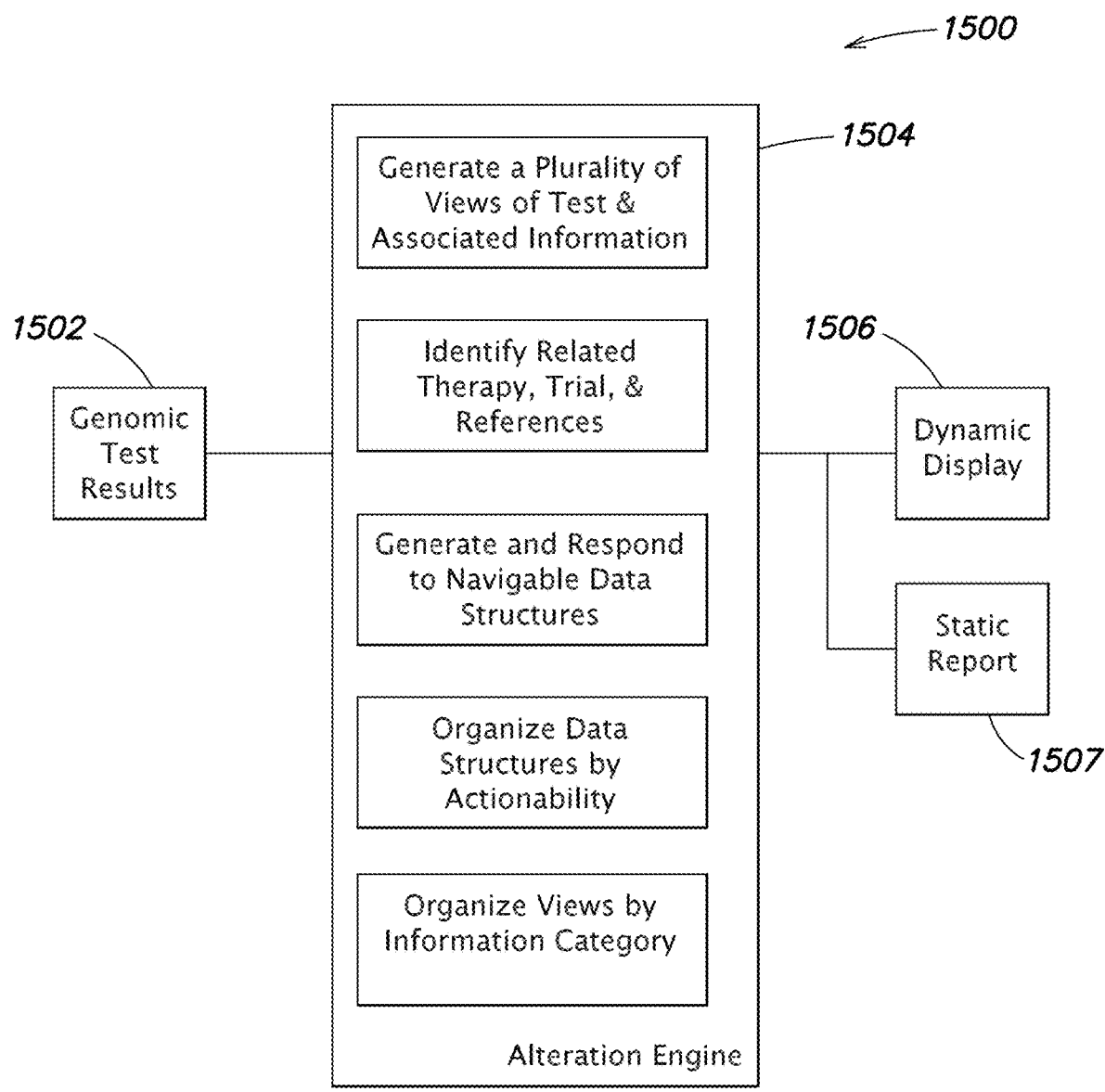
FIG. 15 is a diagram of a system for managing genomic testing information using an alteration engine, according to one embodiment.

Referring to FIG. 15, there is illustrated an example of a system 1500 for managing genomic testing information using an alteration engine 1504. Elements of the system 1500 can be provided using a computing system such as the computer system 500 and/or 502 described with reference to FIG. 5. For example, the alteration engine 1504 can be executed on the computer system 500 and/or 502 to provide the functions and operations discussed herein. In other embodiments, the alteration engine 1504 can include additional components executed on the computer system to perform specific operations.

As shown in FIG. 15, various embodiments of the alteration engine 1504 are configured to accept genomic test results 1502 and associate the genomic test results with curated information. The curated informing can include detailed analysis or additional information tailored to the characteristic of the test results. For example, the test results generated for a specific patient can specify a plurality of genes and alterations found within the patient's cancer. The alteration engine 1504 can be configured to associate curated information tailored to the specific genes/alteration identified for the patient.

In some embodiments, the alteration engine 1504 can be configured to generate a single source display of the test results, curated information, and any additional information as a dynamic display 1506. The dynamic display 1506 can include and organize the test results, the curated information, and the additional information to minimize the volume of data displayed to the user at any one time. According to one embodiment, the dynamic display 1506 can include a plurality of views of the test results, the curated information, and the additional information. In one example, the test, curated, and additional information can be organized into categories for display in a user interface. In some embodiments, the user interface can be specially configured for navigation with mobile devices.

The user interfaces generated by the system can also be configured to include gene and alteration information specific to a current patient being viewed. The user interfaces are configured to present categorized information to facilitate understanding of the gene and alteration information for the current patient. In one example, the dynamic display is presented for a specific patient selected by the user from a patient listing. Once selected, the current patient's information (e.g., name, date of birth, height, weight, sex, patient id, case id, etc.) can be provided along with information regarding the genetic testing conducted (e.g., specimen receipt date, report generation date, diagnosis (type of tumor), collection date for specimen, collection method, specimen type, etc.) as a first portion of a dynamic display 1506.

A second portion of the dynamic display 1506 generated by the system and/or alteration engine 1504 can include the results of the genetic testing organized by gene and alteration. In some embodiments, the alteration engine 1504 can include a user interface ("UI") component configured to generate and to provide for navigation within the dynamic display 1506. For example, each gene and alteration result generated from genomic testing of the current patient's cancer can be displayed as its own data structure. The data structure can contain selectable indicators of actionable information specific to each of the gene/alteration results. In one embodiment, the UI component is configured to transition the dynamic display 1506 to the actionable information in response to selection of the indicators.

According to one embodiment, each gene/alteration data structure is referred to as a brick. Each brick includes a display title or name for an associated gene and alteration. The display may include a section of dynamic display containing a first and second portion. The second portion of the display includes the gene/alteration data structures ("bricks"). An example brick may include, in the display, a title for a gene/alteration identified by the genomic testing.

The alteration engine 1504 and/or UI component can be configured to arrange the bricks responsive to actionable information associated with each brick. For example, bricks having associated therapy information can be given precedence in a display of the test results at 704 over bricks without associated therapy information. Further bricks having associated clinical trials can be given precedence in the display over bricks without associated trial information. In further examples, the number of information items within each category can be used to establish a display precedence based on the categories of actionable information (e.g., therapy, trial, reference). In some embodiments, indicators are generated specific to the category of actionable information.

According to some embodiments, actionable information refers to the presence of information diagnostically relevant to a gene or alteration. For example, actionable information can be reviewed by the user (e.g., a physician) to inform treatment decisions for that patient, to facilitate the physician's determinations regarding the patient's cancer, or to educate the physician on the gene/alteration, among other options. The actionable information can also be relevant to patient's tumor type as well as the gene and alteration. Each brick may include a navigable indicator reflecting available actionable information. In one embodiment, the display of bricks can be ordered based on actionability, wherein actionability can be defined on available information for an FDA approved agent in the patient's tumor type, available information for an FDA approved agent in another tumor type, and/or available information for a mechanistically driven or biologically relevant clinical trial based on the alteration(s) found. In addition, each brick can include a title display reflecting a specific gene and alteration associated with each brick that can be navigated to additional, and/or actionable information regarding the gene and alteration.

In some embodiments, the brick of information for each gene alteration can include information on the gene and the alteration, where additional information is visualized responsive to a hover action. In one example, the number of therapies trials and references can be visualized responsive to user interface pointer hovering over the gene/alteration brick.

In some embodiments, actionable information can be grouped by the system based on categories or source, and indicators can be generated according to any such groupings. For example, the system can group information on available therapies (e.g., therapy indicator or tag), clinical trials (e.g., trial indictor or tag), and in further examples, publications referencing the gene and/or alteration can also be grouped by the system in the dynamic display. Each indicator can be displayed separately for each brick associated with a gene and alteration. The indicators are configured to transition the user to one or more information items associated with the displayed gene/alteration. By selecting the therapy indicator, the user transitions the system to matching therapy information items. In some embodiments, the brick can also include an indicator or tag reflecting that updated information is available in any one or more of the associated therapy, trial, and reference information items.

Each gene and alteration is associated with interpreted statements that provide contextual information regarding the gene/alteration. The contextual information can include, for example, the expression of the gene (e.g., a resulting protein), related genes, genomic family, etc. The interpreted statements can also provide information on frequency of the alteration (e.g., in the general population or a study population), information on related genes/alterations, related therapies, or related clinical trials. In some embodiments, the interpreted statements are included as "curated" information that summarizes and/or provides current medical knowledge and/or analysis of the gene and alteration, whether the knowledge matches the specific tumor type for the patient or not. The curated information can be generated and stored on the system for access by the alteration engine 1504 and/or the UI component.

In some embodiments, the alteration engine 1504 is configured to generate curated information from various knowledge bases (e.g., ClinicalTrials.gov, PubMed, journal publications, etc.). In one embodiment, the alteration engine 1504 can include a curation component configured to capture genomic information for curation. In some embodiments, the alteration engine 1504 captures online resources (e.g., clinical studies, journal publications, research documents, academic articles/resource, etc.) pertaining to any one or more of tumor, gene, and alteration. The alteration engine 1504 and/or curation component can be configured to present the captured information to a human curator, who creates interpreted statements from the available information. In some embodiments, the alteration engine 1504 can be configured to summarize or synthesize online resources into automatically generated interpreted statements. In one embodiment, the alteration engine 1504 and/or curation component can be configured to present such interpreted statements to human curators for approval or editing prior to use on the system. In one embodiment, the curation component can automatically identify information items for curation based on keywords (e.g., keywords for tumor type, gene, alteration, and/or therapy). In some implementations, the curation component can parse and capture content from the identified information items. The captured content can be presented to, for example, the human curators for revision and/or approval.

According to one embodiment, each information item within the drawer can include a navigation option to provide further detail on a selected information item. For example, a row for ERBB3/amplification can be selected in the user interface to transition the system to a detailed view of information on the ERBB3 gene and amplification alteration for the patient's tumor type. In another example, the alteration engine 1504 and/or UI component can generate a hyperlink or other navigable element provided in the dynamic display to transition the system to the detailed view.

In one embodiment, a detailed view of the gene/alteration/tumor combination may be provided within the interface. The detailed view can include the interpreted statements shown for the gene and alteration. Further, the detailed view can also include navigation options for transitioning the system to related genomic information. Responsive to selection, expandable display elements can each be independently expanded to provide navigation options. Each navigation option can be grouped according to a respective information source. In some embodiments, the expandable display elements can include an indicator of a number of information items within each group.

According to some embodiments, the alteration engine 1504 is configured to identify related information for inclusion in the dynamic display 1506 and associated views. In one example, the alteration engine 1504 can include an analytic subsystem configured to identify matches between tumor type, gene, and/or alteration and includes the matching information items according to display drawers. Identification of related information by the analytic subsystem can be employed by the alteration engine 1504 and/or the UI component to generate the indication of the number of information items associated with each display drawer and/or in the detailed view expandable elements. In some examples, the analytic subsystem and/or alteration engine 1504 can maintain counts for each information item within system categories (e.g., therapy, trial, references) and store that information for access within each patient's genomic test report or in a detailed information screen.

As discussed above, the dynamic display 1506 is configured to provide multiple paths to genomic alteration information, actionable information, and specific information items or views. In some embodiments, the path taken through the dynamic display 1506 can impact how the system displays any information within a given view. For example, expansion of one of the drawers provides access to the information items within each group. According to one embodiment, successive selection of another drawer can be configured to close any open drawer as well as to transition the dynamic display to the expanded view of the selected drawer. Further, responsive to selection of a drawer within the dynamic display, each information item within a specific drawer is presented. If the information items within a drawer are accessed from a link displayed in a brick from the second portion of the dynamic display, then the information items associated with the link (i.e., therapies associated with the ERBB3 gene are highlighted to facilitate review). The system and/or alteration engine 1504 can be configured to highlight such associated information items within any drawer accessed when shown in their respective expanded views.

Example Genomic System

Figure 16:
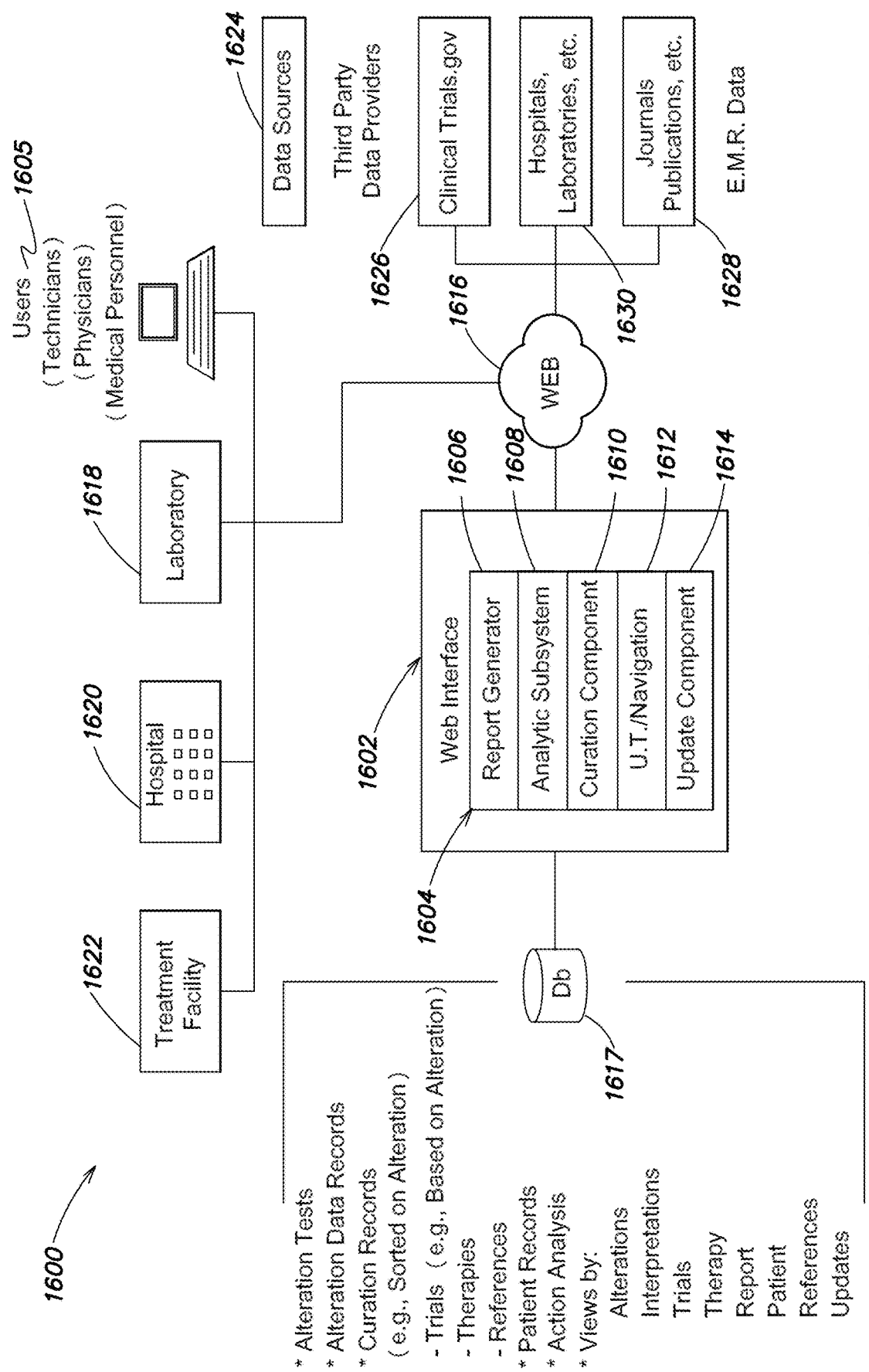
FIG. 16 is a diagram of a system for managing genomic testing information, according to one embodiment.

FIG. 16 shows an example embodiment of a system 1600 for managing genomic testing information. The system 1600 can be configured to provide a single reporting source for accessing and applying available information on a patient's cancer. According to some embodiments, genomic testing on the patient's cancer provides specific information the tumor, one or more genes implicated by the tumor, and one or more alterations within the genes which can be displayed by the system 1600 through a web interface 1602. In some embodiments, the web interface 1602 can include an alteration engine 1604 that performs any of the operations discussed above with respect to the alteration engine 104. For example, the web interface and/or alteration engine 1604 can be configured to use the testing information on tumor, gene, and alteration for a patient to manage delivery of curated information to end users (e.g., technicians, physicians, medical personal, etc., at 1605) over a communication network 1616. In one embodiment, the alteration engine 1604 can include a UI or navigation component 1612 configured to generate displays that focus users (e.g., physicians) on actionable information within the genomic test results and associated information. For example, the UI component 1612 can display navigable data structures including information on genes and alterations identified in a genomic test coupled with indicators informing the user of available actionable information associated with a patient's cancer.

According to some embodiments, the alteration engine 1604 can include specific component for providing specific functionality on the web interface 1602. For example, the alteration engine 1604 can also include a report generator component 1606 configured to generate physical and/or static report for downloading through the web interface. The alteration engine 1604 can also include an analytic subsystem 1608 an analytic subsystem configured to identify matches information between a current patient's tumor type, gene, and/or alteration and include or identify the matching information items for display in the patient's test results.

According another embodiment, the alteration engine can also include a curation component 1610 configured to generated curated information for use on the system. The curated information can include interpreted statements regarding any one or more of genomic alterations, an implicated gene, a patient's tumor type, and/or potentially applicable therapies for a patient's cancer. In some examples, the curation component can be accessed by human operators "curators" who generate and/or approve system generated interpreted statement regarding genomic alterations, an implicated gene, a patient's tumor type, and/or potentially applicable therapies.

As discussed, the alteration engine can also include the UI component 1612 configured to generate and display navigable data structures (e.g., bricks and drawers) which include information on genes and alterations identified in a genomic test, which can be coupled with indicators for actionable information associated with a patient's cancer. The UI component 1612 can transition the system to the actionable information (e.g., therapy information items, trial information items, reference information items) responsive to selection in the user interface.

In further embodiments, the alteration engine can include an update component 1614 configured to track any updates to genomic alterations and any information associated with the genomic alterations. In one embodiment, the update component 1614 can identify updates information for display by the UI component 1612. Various embodiments, of the alteration engine components are configured to perform the function and operations discussed above with respect to the alteration engine 104 and associated components.

According to some embodiments, the web interface 1602 can be accessed by users (e.g., 1605) over the internet. The user can access the web interface from a variety of location (e.g., laboratory 1618, hospital 1620, and treatment facility 1622). In various embodiments, the users at any one or more of 1618-1622 can share genomic test reports with each other. For example, the web interface 1602 can be configured to provide social functions between users. In some embodiments, the web interface can limit sharing to practice groups, within treatment facilities, or within medical institutions (e.g., hospitals). According to one aspect, sharing of test results and associated genomic information on patients can create a strong community of physicians, and foster discussion about treatment or even specific patients.

According to some embodiments, the web interface 1602 stores genomic test information in database 1617. Database 1617 is illustrated as a single database, but in other embodiments, database 1617 can include any storage medium or organizational unit for storing and accessing genomic test results and associated information. Further embodiments can include a plurality of databases and can also include distributed data architectures. According to one embodiment, database 1617 can include a variety of data records accessed by the web interface 1602 to manage delivery of genomic test results and associated information.

For example, the database can include information on genomic testing. In one example, genomic test results are stored and associated with patient records. The genomic test results can include information on genomic alterations. Specific genomic alterations can be stored in database 1617 and access for presenting information within a display of a patient's test report. The database can include curation records stored and associated with any one or more of a tumor type, gene, and/or genomic alteration. Information on clinical trial can likewise be stored as information items associated with any one or more of a tumor type, gene, and/or genomic alteration. The database 1617 can also store therapy information and references information and provide associated for either to any one or more of a tumor type, gene, and/or genomic alteration. The database 1617 can also be configured to track and store information on updates to any information within the database. In one example, updates can be flagged by other system components and the flags resolved or remove once viewed.

In further embodiments, the database can store information on data views for used by web interface and/or the UI component 1612. The views can include, for example, alteration views, genomic interpretation views, clinical trial views, therapy views, static report views, patient record views, references views, and updates views. Each one or more of the views can be accessed and used by the web interface to present information on genomic testing and associated information to a user. In some examples, the system and/or web interface can be configured to capture information from external information sources for storage in database 1617. In one example, external data source 1624 can contain information related to a patient's tumor type, gene, and/or alteration. The information from the external information can be captured and stored as records in database 1617 accessible via the relationship to the tumor type, gene, and/or alteration.

According to some embodiments, the information stored in database 1617 can include reference to the external information source. For example, clinical trial information items can include links to clinicaltrials.gov 1626, reference information items can include links to PubMed.gov (e.g., 1628). In further embodiments, the web interface 1602 can be configured to access genomic alteration information for cancer diagnoses made at a hospital or laboratory (e.g., 1630). For example, the web interface can capture genomic information from EMR (electronic medical records) to retrieve tumor type, implicated gene, and/or alteration type for storage in database 1617. In some implementations, references or links to the specific medical records can also be stored in the database. In one example, the links to the medical records can be presented in a dynamic display generated on system 1600.

According to one aspect, the database 1617 and all associated information can be organized or accessed based on one or more of tumor type, gene, and alteration. In one embodiment, the tumor type, gene, and alteration data is stored as a data unit (e.g., a tuple). The data unit can be used by the system to identify or display related information based on matching any one or more of the tumor type, gene, and alteration. In further embodiments, each data unit can be linked to actionable information (where it exists). For example, each data unit can be linked to a matching therapy (e.g., a therapy information item describing a specific therapy, application, etc.). In another example, data units can be linked to a matching clinical trial (e.g., stored as a clinical trial information item).

According to one embodiment, the information in the database associated with tumor, gene, or alteration provides insight into prescribed uses of therapies (on-label) and off-label applications for such therapies. In one example, off-label uses can be identified based on alteration (e.g., different tumors but same alteration—provides relation information on a potentially effective therapy for the current patient's cancer.)

According to another embodiment, each record can be associated with a data space for an update flag. Responsive to any update to information on the database 1617, the system can enter information in the data space for the update flag. Tracking updates to genomic alteration and associated information facilitates user awareness of potential significant changes in a patient report. Further, tracking of update information in the database 1617 enables the system to deliver notification regarding any updates.

In some further embodiment, social functions can have associated records in the database. For example, permission information (e.g., who can share a report and/or who can receive a shared report) can be associated with test reports stored in database 1617.

Figure 17:
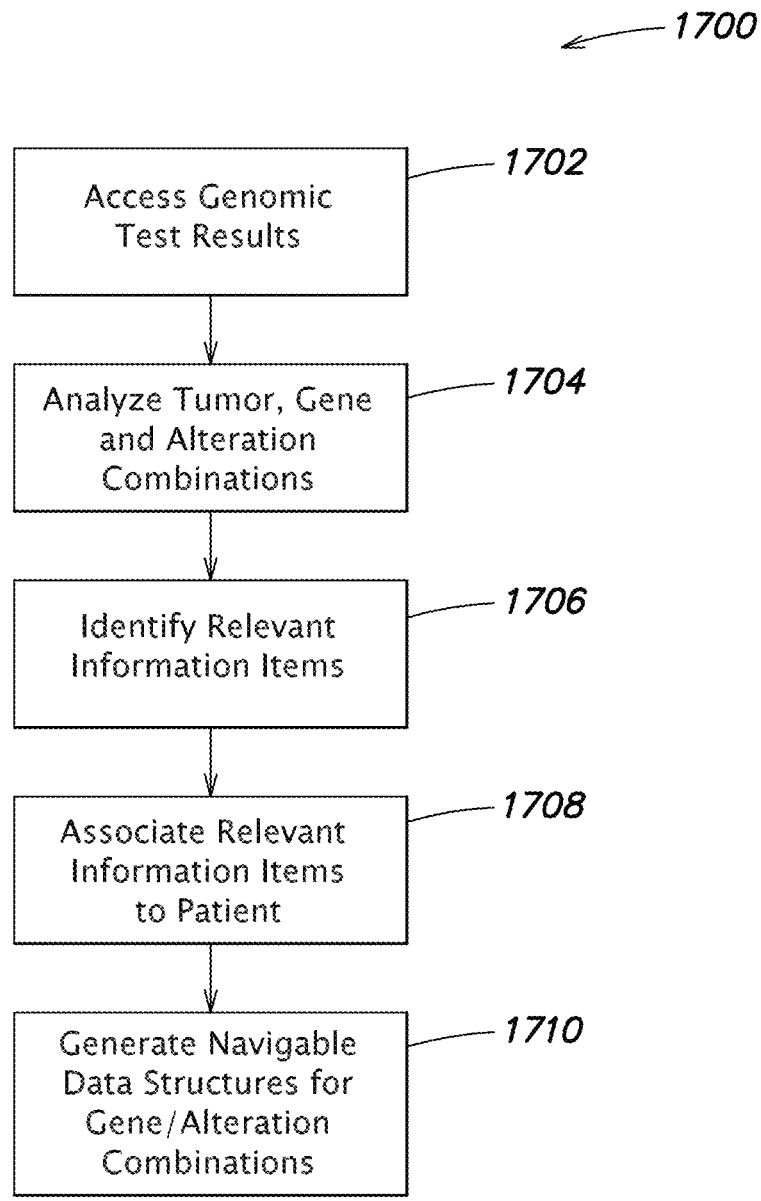
FIG. 17 is an example process flow for a method of managing genomic testing information, according to one embodiment.

According to some embodiments, the web interface 1602 can implement a variety of function and processes for managing delivery of genomic test results and any associated information. Shown in FIG. 17 is an example process flow 1700 for managing genomic testing information. The process 1700 begins at 1702 with access to genomic test results. According to one embodiment, genomic test results include information specific to a patient's tumor type, one or more genes implicated by the tumor, and alteration type associated with the one or more gene. At 1704, the tumor type, gene, and alteration combinations for the patient's cancer are analyzed, and relevant information items are identified at 1706.

In some embodiments, the relevant data items can include clinical trials that match on any one or more of tumor type, gene, and alteration. The relevant data items can also include therapies or references that match on tumor, gene, and/or alteration. In some example, the relevant data items are stored for analysis at 1704 based on activity of curators. In one example, human curators can review clinical trial information (e.g., criteria, gene/alteration target, trial therapy, trial drug) and associate that clinical trial information with tumor types, genes, and/or alterations. The human curators can also review and characterize information on therapies and reference for use in, for example, process 1700.

Once relevant information is identified, for example, at 1706, any relevant information item can be associated with the patient having the matching tumor type, gene, and/or alteration at 1708. The association(s) defined at 1708 can be used at 1710 to generate navigable data structures which can be configured to organize gene and alteration combinations and links to any associated relevant information (e.g., identified at 1706 and associated at 1708). In some embodiments, the navigable data structures can be presented in the user interface display.

In other embodiments, the relevant information identified at 1706 can be associated with patient records and/or specific genomic tests at 1708 based on a specified data model. Further, association of the relevant information at 1708 can include generation and storage of the associated information a data unit (e.g., information item) and the data unit can then be associated with the patient, and/or a gene or alteration in the patients genomic test results through a navigation link. The navigation link can be used as part of a dynamic display for a specific gene/alteration combination. Responsive to selection of the link, the dynamic display can transition to the relevant information.

Figure 18A:
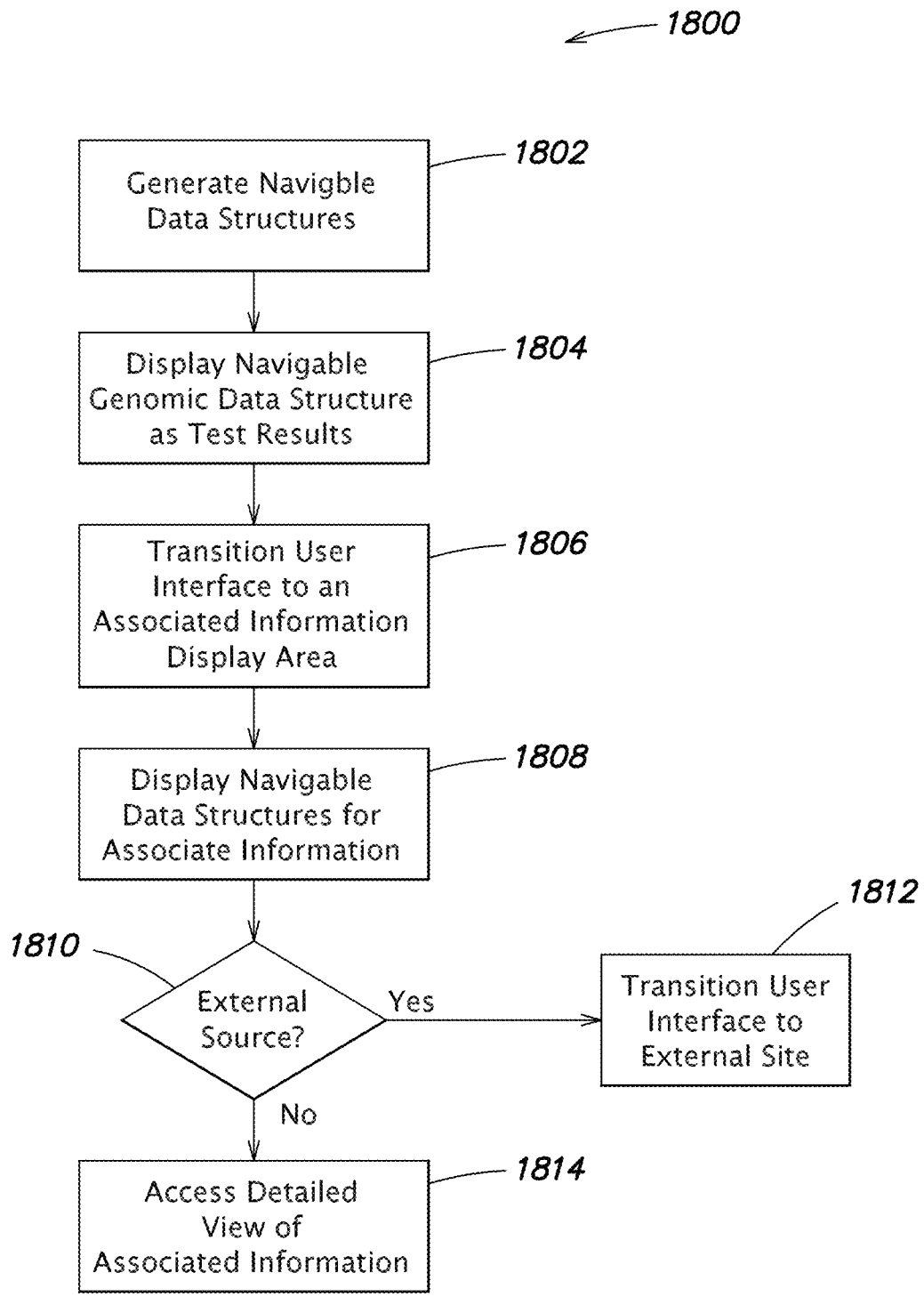
FIG. 18A is an example process flow for a method of navigating genomic testing information, according to one embodiment.

Shown in FIG. 18A is an example process 1800 for navigating through genomic testing information. The process 1800 begins at 1802 with generation of navigable data structures. In some embodiments, the navigable data structures can be generated by other processes (e.g., process 1700) and accessed at 1802 rather than being generated at 1802. The navigable data structures can be generated or accessed based on genomic test results for a current patient. In one embodiment, a genomic data structure is generated or accessed for each genomic alteration identified in the current patient's cancer cells. In other embodiments, navigable data structures can be accessed or generated for any associated information relevant to each genetic alteration at 1802. In some examples, the associated information can include relevant therapies, relevant clinical trials, and/or relevant references.

At 1804, each genomic data structure is displayed. The genomic data structures can be displayed in a first portion of a user interface. Each of the genomic data structures is configured to access associated information relevant to the genomic alteration stored as part of the genomic data structure. For example, each genomic data structure includes specification of a gene (e.g., by name) and an alteration type for the gene found in the patient's cancer cell. At 1806, responsive to selection of one of the genomic data structures, the user interface transitions to an associated information display area. In some embodiments, the associated information display area can include organization of associated information data structures by information type. In some examples, the organization by information type includes drawers for each type configured to expand upon access to the contents (and type) organized within the drawer. Depending on the selection within the genomic data structure, the transition to the associated information display area can include a transition to a specific category of information (e.g., genomic alternation interpretations, therapies, clinical trials, references, and updates). Within the associated information display area, associated information data structures are displayed at 1808.

Each of the associated information data structures can also be navigable. Responsive to selection of the associated information data structures, the user interface can transition to additional information on the selected associated information data structure. The transition invoked depends on the source/target of the associated information data structure. If the associated information structure includes an external target, for example, an external website, selection of the external information source at 1810 YES, results in a transition of the user interface to the external site at 1812. In one example, the external site can include ClinicalTrials.gov or PubMed.gov, among other options.

If the target of the associated information data structure is not external 1810 NO, selection of the associated information data structure results in a transition to a detailed view of the associated information at 1814. For example, depending on the associated information data structure and/or a target selected within the structure, the transition can be made to a detailed view of therapy information (e.g., FIG. 7G) or a detailed view of a gene/alteration combination (e.g., FIG. 7E).

According to some embodiments, process 1800 is intended for successive execution to transition between and within genomic data structures, associated information data structures, detailed views, and external information locations. For example, steps 1806-1808 can be repetitively executed for each one of a plurality of genomic data structures and/or steps 1808-1814 can be repetitively executed to access each one or some of a plurality of associated information data structures.

Further, either process 1800 or 1700 can be executed on various systems or can be executed by various system components.

Figure 18B:
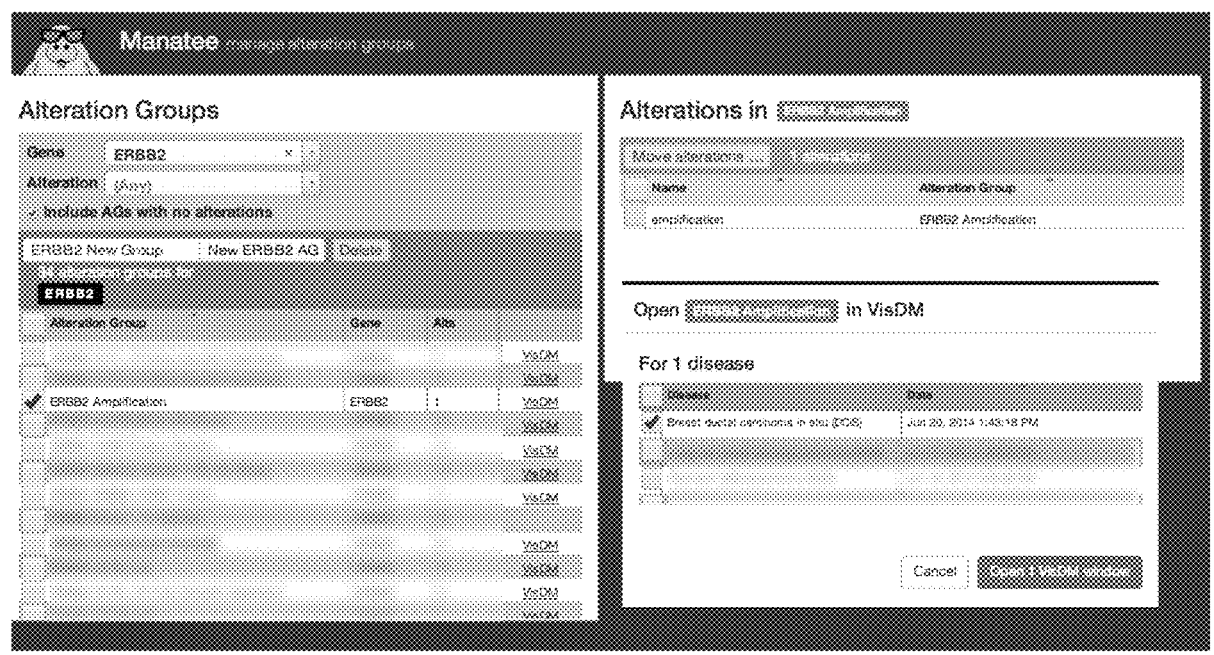
FIGS. 18B-C show example interfaces that may be used with a data model according to various embodiments of the present invention.
Figure 18C:
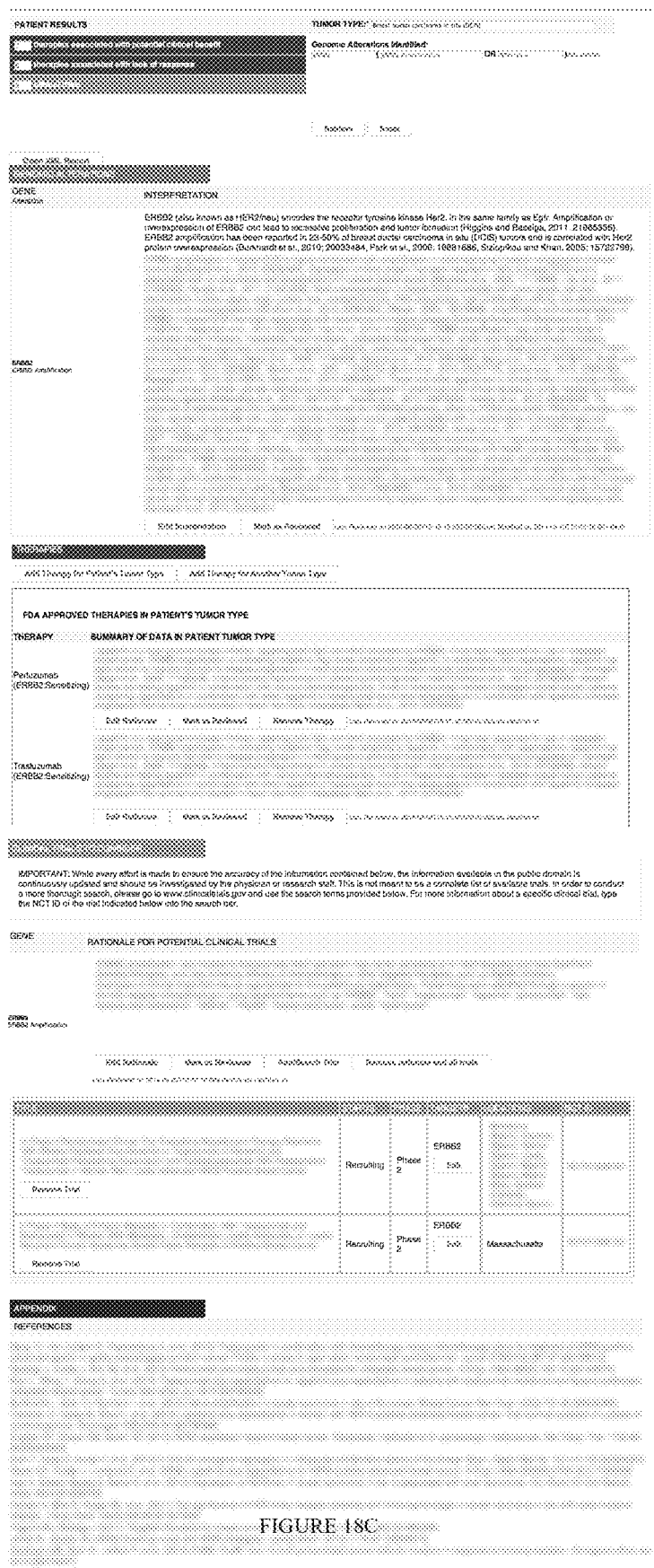

FIGS. 18B-18C show various example interfaces that may be used in accordance with various embodiments of the present invention. Such interfaces may provide functionality to a user in relation to the data model provided above. For instance, as shown in FIG. 18B, a user opens an application to view what alteration groups are available. For instance, in one example interface, a user may be permitted to select a gene, causing alteration groups to be displayed. When a user selects an alteration group, alterations are displayed and a link to open DAGAs connected to that alteration group is displayed within the interface.

As shown in FIG. 18C, once the user selects the DAGA (disease+alteration group) the user would like to view, an application interface opens including all of the content for that DAGA, including an interpretation of the alteration in the context of the disease, a set of therapies and clinical trials relevant for any patient with that disease and any alteration in that alteration group, and appropriate journal references and other citations supporting those actionable elements.

Example Computer Systems

Various aspects, functions, components, and/or processes described herein may be implemented as hardware, software, or a combination of hardware and software on one or more computer systems. There are many examples of computer systems currently in use. Some examples include, among others, network appliances, personal computers, workstations, mainframes, networked clients, servers, media servers, application servers, database servers, web servers, and virtual servers. Other examples of computer systems may include mobile computing devices, such as cellular phones and personal digital assistants, and network equipment, such as load balancers, routers and switches. Additionally, aspects in accord with the present invention may be located on a single computer system or may be distributed among one or more computer systems connected to one or more communication networks.

For example, various aspects and functions may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Thus, the invention is not limited to executing on any particular system or group of systems. Further, aspects may be implemented in software, hardware or firmware, or any combination thereof. Thus, aspects in accord with the present invention may be implemented within methods, acts, systems, system placements and components using a variety of hardware and software configurations, and the implementation is not limited to any particular distributed architecture, network, or communication protocol. Furthermore, aspects in accord with the present invention may be implemented as specially-programmed hardware and/or software.

Figure 19:
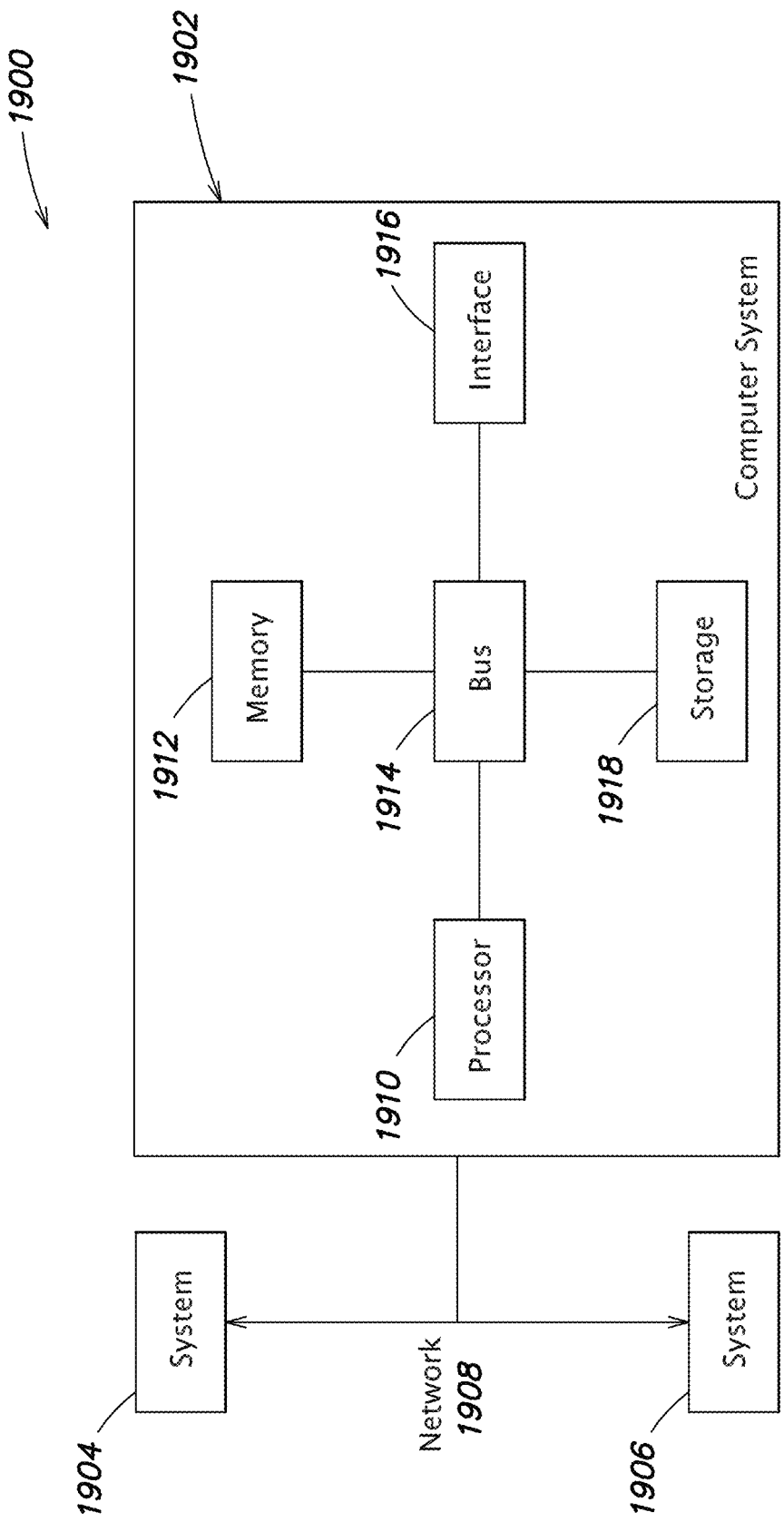
FIG. 19 is a block diagram of one example of a computer system that may be used to perform processes and functions disclosed herein.

FIG. 19 shows a block diagram of a distributed computer system 1900, in which various aspects and functions in accord with the present invention may be practiced. The distributed computer system 1900 may include one or more computer systems. For example, as illustrated, the distributed computer system 1900 includes three computer systems 1902, 1904 and 1906. As shown, the computer systems 1902, 1904 and 1906 are interconnected by, and may exchange data through, a communication network 1908. The network 1908 may include any communication network through which computer systems may exchange data. To exchange data via the network 1908, the computer systems 1902, 1904, and 1906 and the network 1908 may use various methods, protocols and standards including, among others, token ring, Ethernet, Wireless Ethernet, Bluetooth, TCP/IP, UDP, HTTP, FTP, SNMP, SMS, MMS, SS7, JSON, XML, REST, SOAP, CORBA HOP, RMI, DCOM and Web Services.

Computer systems 1902, 1904 and 1906 may include mobile devices such as cellular telephones, tablets, touch screen devices, etc. The communication network may further employ one or more mobile access technologies including 2nd (2G), 3rd (3G), 4th (4G or LTE) generation radio access for cellular systems, WLAN, Wireless Router (WR) mesh, and other communication technologies. Access technologies such as 2G, 3G, 4G and LTE and future access networks may enable wide area coverage for mobile devices. For example, the network may enable a radio connection through a radio network access such as Global System for Mobil communication (GSM), General Packet Radio Services (GPRS), Enhanced Data GSM Environment (EDGE), Wideband Code Division Multiple Access (WCDMA), among other communication standards. Network may include any wireless communication mechanism by which information may travel between the devices 1904 and other computing devices in the network.

To ensure data transfer is secure, the computer systems 1902, 1904 and 1906 may transmit data via the network 1908 using a variety of security measures including TSL, SSL or VPN, among other security techniques. While the distributed computer system 1900 illustrates three networked computer systems, the distributed computer system 1900 may include any number of computer systems, networked using any medium and communication protocol.

Various aspects and functions in accord with the present invention may be implemented as specialized hardware or software executing in one or more computer systems including the computer system 1902 shown in FIG. 19. As depicted, the computer system 1902 includes a processor 1910, a memory 1912, a bus 1914, an interface 1916 and a storage system 1918. The processor 1910, which may include one or more microprocessors or other types of controllers, can perform a series of instructions that manipulate data. The processor 1910 may be a well-known, commercially available processor such as an Intel Pentium, Intel Atom, ARM Processor, Motorola PowerPC, SGI MIPS, Sun UltraSPARC, or Hewlett-Packard PA-RISC processor, or may be any other type of processor or controller as many other processors and controllers are available. As shown, the processor 1910 is connected to other system placements, including a memory 1912, by the bus 1914.

The memory 1912 may be used for storing programs and data during operation of the computer system 1902. Thus, the memory 1912 may be a relatively high performance, volatile, random access memory such as a dynamic random access memory (DRAM) or static memory (SRAM). However, the memory 1912 may include any device for storing data, such as a disk drive or other non-volatile storage device, such as flash memory or phase-change memory (PCM). Various embodiments in accord with the present invention can organize the memory 1912 into particularized and, in some cases, unique structures to perform the aspects and functions disclosed herein.

Components of the computer system 1902 may be coupled by an interconnection element such as the bus 1914. The bus 1914 may include one or more physical busses (for example, busses between components that are integrated within a same machine), and may include any communication coupling between system placements including specialized or standard computing bus technologies such as IDE, SCSI, PCI and InfiniBand. Thus, the bus 1914 enables communications (for example, data and instructions) to be exchanged between system components of the computer system 1902.

Computer system 1902 also includes one or more interfaces 1916 such as input devices, output devices and combination input/output devices. The interface devices 1916 may receive input, provide output, or both. For example, output devices may render information for external presentation. Input devices may accept information from external sources. Examples of interface devices include, among others, keyboards, mouse devices, trackballs, microphones, touch screens, printing devices, display screens, speakers, network interface cards, etc. The interface devices 1916 allow the computer system 1902 to exchange information and communicate with external entities, such as users and other systems.

Storage system 1918 may include a computer-readable and computer-writeable nonvolatile storage medium in which instructions are stored that define a program to be executed by the processor. The storage system 1918 also may include information that is recorded, on or in, the medium, and this information may be processed by the program. More specifically, the information may be stored in one or more data structures specifically configured to conserve storage space or increase data exchange performance. The instructions may be persistently stored as encoded signals, and the instructions may cause a processor to perform any of the functions described herein. A medium that can be used with various embodiments may include, for example, optical disk, magnetic disk or flash memory, among others. In operation, the processor 1910 or some other controller may cause data to be read from the non-volatile recording medium into another memory, such as the memory 1912, that allows for faster access to the information by the processor 1910 than does the storage medium included in the storage system 1918. The memory may be located in the storage system 1918 or in the memory 1912. The processor 1910 may manipulate the data within the memory 1912, and then copy the data to the medium associated with the storage system 1918 after processing is completed. A variety of components may manage data movement between the medium and the memory 1912, and the invention is not limited thereto.

Further, the invention is not limited to a particular memory system or storage system. Although the computer system 1902 is shown by way of example as one type of computer system upon which various aspects and functions in accord with the present invention may be practiced, aspects of the invention are not limited to being implemented on the computer system, shown in FIG. 19. Various aspects and functions in accord with the present invention may be practiced on one or more computers having different architectures or components than that shown in FIG. 19. For instance, the computer system 1902 may include specially-programmed, special-purpose hardware, such as for example, an application-specific integrated circuit (ASIC) tailored to perform a particular operation disclosed herein. Another embodiment may perform the same function using several general-purpose computing devices running MAC OS System X with Motorola PowerPC processors and several specialized computing devices running proprietary hardware and operating systems.

The computer system 1902 may include an operating system that manages at least a portion of the hardware placements included in computer system 1902. A processor or controller, such as processor 1910, may execute an operating system which may be, among others, a Windows-based operating system (for example, Windows NT, Windows 2000/ME, Windows XP, Windows 7, or Windows Vista) available from the Microsoft Corporation, a MAC OS System X operating system available from Apple Computer, one of many Linux-based operating system distributions (for example, the Enterprise Linux operating system available from Red Hat Inc.), a Solaris operating system available from Sun Microsystems, or a UNIX operating systems available from various sources. Many other operating systems may be used, and embodiments are not limited to any particular operating system.

The processor and operating system together define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, functions in accord with aspects of the present invention may be implemented using an object-oriented programming language, such as JAVA, C++, Ada, or C# (C-Sharp). Other object-oriented programming languages may also be used. Alternatively, procedural, scripting, or logical programming languages may be used.

Additionally, various functions in accord with aspects of the present invention may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed placements, or any combination thereof. For example, a web page may be implemented using HTML while a data object called from within the web page may be written in C++. Thus, the invention is not limited to a specific programming language and any suitable programming language could also be used.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

In some embodiments, genomic alteration, tumor type, and treatment can be stored as a tuple in a database. The tuple can be associated with information on the affected gene. In some examples, the database can include records for tumor type, treatment, and gene/alteration combinations, stored as a data unit. In other embodiments, the database can be indexed on any one or more of alteration, affected gene or pathway, tumor type, and treatment to speed retrieval of outcome data associated with those data records. In further embodiments, an outcome tracking and analysis system can include a data model based, at least in part, on organizing patient, outcome, and treatment data using alteration or affected gene or pathway information.

In some embodiments, the data model can reduce such treatment information to system specified categories for one or more therapies applied. For example, data input by a user can exclude dosing information, patient demographic information, etc. In other examples, the system can include user interface elements for inputting dosing information, patient specific information, etc., as optional information. In further embodiments, the system can request and/or require more specific information regarding treatment (dose, frequency, duration, patient weight, height, age, or any other patient factor that impacts a dosing regimen).

According to another embodiment, the data model is configured to simplify outcome information inputs. In one example, the data model defines outcome information as one of progressive, stable, partial response, and complete response. The user can input outcome information based on selection of the defined outcomes, simplifying any data entry by users. Further, treatment and outcome information can be captured from third-party information sources and stored according to the data model. According to some embodiments, any data source for treatment and outcome information can be converted into information retrievable on any one or more of alteration, affected gene or pathway, tumor type, and a specified treatment. In further embodiments, additional information on treatment, outcomes, tumor type, affected gene or pathway, genomic alterations can be stored according to the data model. The additional information can be associated with patients, and accessed from any defined patient group. In one example, a patient group can be selected according to user input of any one or more of alteration, affected gene or pathway, tumor type, and treatment. The system can enable selection within any specified patient group to access any additional detail information associated with any patient with the patient group.

In some embodiments, the system can generate and display outcome and treatment information according to the data model. For example, visual displays organizing treatment and outcome information according to genomic alternation, affected gene or pathway, tumor type and treatment can be generated and displayed by the system. The system can be configured to respond to selection within of any of the visual display categories to navigate or filter within the treatment and outcome information. Selection within patient groups can also trigger transitions to detailed views of treatment and outcome information associated with specific patients.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A system for managing delivery of genomic information, the system comprising: at least one processor operatively connected to a memory, the at least one processor when executing is configured to:

collect biomarker data and store the biomarker data in the memory;

receive patient-specific pathology information of a plurality of patients, wherein the patient-specific pathology information comprises a genomic alteration and a disease relating to each patient of the plurality of patients and store the patient-specific pathology information in the memory;

at a first time, generate a graph-based data structure that includes the biomarker data and the patient-specific pathology information by:

generating a plurality of patient nodes representing the plurality of patients;

generating a plurality of alteration nodes representing genomic alterations of the plurality of patients;

generating a plurality of alteration group (AG) nodes representing a plurality of AGs;

generating a plurality of actionable item nodes representing a plurality of actionable items, wherein each actionable item node of the plurality of actionable item nodes represents one or more actionable items of the plurality of actionable items;

generating a first plurality of tuples, each tuple of the first plurality of tuples comprising:
- a corresponding patient node of the plurality of patient nodes; and
- a corresponding alteration node of the plurality of alteration nodes;

generating a second plurality of tuples, each tuple of the second plurality of tuples comprising:
- a corresponding alteration node of the plurality of alteration nodes; and
- a corresponding AG node of the plurality of AG nodes;

generating a plurality of disease alteration group association (DAGA) nodes, each DAGA node of the DAGA nodes associating:
- a corresponding relationship associated with a corresponding AG node of the plurality of AG nodes and a corresponding disease, with
- a corresponding actionable item node of the plurality of actionable item nodes:

at a second time, recompute a topology of the graph-based data structure by at least merging at least two AG nodes sharing a same actionable item node into a new AG node;

traverse the recomputed graph-based data structure to obtain a path for a patient of the plurality of patients, wherein the path starts from a patient node representing the patient and ends with a final actionable item node; and provide one or more actionable items represented by the final actionable item node.

2. The system according to claim 1, wherein the plurality of actionable items includes at least one of a group comprising a recommendation for an enrollment of the patient in a clinical trial and a recommendation for a therapy to be applied to the patient.

3. The system according to claim 1, wherein the patient-specific pathology information of the plurality of patients includes at least one of a group comprising disease phenotype information and genetic alteration information.

4. The system according to claim 1, wherein at least one tuple in the graph-based data structure comprises at least two elements connected by a relation.

5. The system according to claim 1, wherein the graph-based data structure further comprises a third plurality of tuples, each tuple of the third plurality of tuples comprising a corresponding patient node of the plurality of patient nodes connected to a corresponding disease through a diagnosis relation.

6. The system according to claim 1, wherein at least one tuple of the graph-based data structure is generated as a result of a genomic test report.

7. The system according to claim 1, wherein at least one tuple of the graph-based data structure is generated as a result of a clinical study.

8. The system according to claim 1, wherein the traversing is performed at least partially by an inference engine.

9. The system according to claim 1, wherein the at least one processor when executing is configured to display an output of the one or more actionable items represented by the final actionable item node to a user of the system.

10. The system according to claim 1, wherein the graph-based data structure includes a resource description framework model (RDF).

11. The system according to claim 1, wherein the graph-based data structure includes a plurality of complex data elements.

12. The system according to claim 11, wherein at least one of the plurality of complex data elements includes a text node element that stores information relevant for precision medicine decision making with respect to a referenced element of the graph-based data structure.

13. The system according to claim 11, wherein at least one of the plurality of complex data elements includes a disease therapy association (DTA) element that associates a disease and a therapy with information relevant to a combination of the disease and the therapy.

14. The system according to claim 11, wherein at least one of the plurality of complex data elements includes a therapy genomic effect (TGE) element that associates a gene targeted by a therapy and a known effect of the therapy.

15. The system according to claim 1, wherein each AG of the plurality of AGs comprises a plurality of gene states.

16. The system according to claim 15, wherein each of the plurality of gene states belongs to a single AG.

17. The system according to claim 15, wherein at least one AG of the plurality of AGs comprises a combination of attributes that defines a unique set of clinically relevant gene states.

18. The system according to claim 1, wherein the at least one processor when executing is configured to propagate information within the graph-based data structure that includes the biomarker data and the patient-specific pathology information.

19. The system according to claim 18, wherein the at least one processor when executing is configured to propagate an FDA approval status within a disease ontology tree associated with the graph-based data structure.

20. The system according to claim 18, wherein the at least one processor when executing is configured to infer relations within the graph-based data structure based on one or more propagation rules.

21. The system according to claim 1, wherein the path comprises at least one tuple having a trust score.

22. The system according to claim 21, wherein the trust score is provided to indicate a likelihood of following the path in the graph-based data structure.

23. The system according to claim 21, wherein the trust score is used to determine the final actionable item node.

24. A computer-implemented method for managing delivery of genomic information, the method comprising:
collecting, by a computer system having a memory, biomarker data and storing the biomarker data in the memory;
receiving, by the computer system, patient-specific pathology information of a plurality of patients, wherein the patient-specific pathology information comprises a genomic alteration and a disease relating to each patient of the plurality of patients and storing the patient-specific pathology information in the memory;
at a first time, determining a graph-based data structure that includes the biomarker data and the patient-specific pathology information by:
generating a plurality of patient nodes representing the plurality of patients;
generating a plurality of alteration nodes representing genomic alterations of the plurality of patients;

generating a plurality of alteration group (AG) nodes representing a plurality of AGs;

generating a plurality of actionable item nodes representing a plurality of actionable items, wherein each actionable item node of the plurality of actionable item nodes represents one or more actionable items of the plurality of actionable items;

generating a first plurality of tuples, each tuple of the first plurality of tuples comprising:
  a corresponding patient node of the plurality of patient nodes; and
  a corresponding alteration node of the plurality of alteration nodes;

generating a second plurality of tuples, each tuple of the second plurality of tuples comprising:
  a corresponding alteration node of the plurality of alteration nodes; and
  a corresponding AG node of the plurality of AG nodes;

generating a plurality of disease alteration group association (DAGA) nodes, each DAGA node associating:
  a corresponding relationship between a corresponding AG node of the plurality of AG nodes and a corresponding disease, with
  a corresponding actionable item node of the plurality of actionable item nodes;

at a second time, recomputing a topology of the graph-based data structure by at least merging at least two AG nodes sharing a same actionable item node into a new AG node;

traversing the recomputed graph-based data structure to obtain a path for a patient of the plurality of patients, wherein the path starts from a patient node representing the patient and ends with a final actionable item node; and provide one or more actionable items represented by the final actionable item node.

25. The method according to claim 24, wherein the plurality of actionable items includes at least one of a group comprising a recommendation for an enrollment of the patient in a clinical trial and a recommendation for a therapy to be applied to the patient.

26. The method according to claim 24, wherein the patient-specific pathology information of the plurality of patients includes at least one of a group comprising disease phenotype information and genetic alteration information.

27. The method according to claim 24, wherein at least one tuple in the graph-based data structure comprises at least two elements connected by a relation.

28. The method according to claim 24, wherein the graph-based data structure further comprises a third plurality of tuples, each tuple of the third plurality of tuples comprising a corresponding patient node of the plurality of patient nodes connected to a corresponding disease through a diagnosis relation.

29. The method according to claim 24, wherein at least one tuple of the graph-based data structure is generated as a result of a genomic test report.

30. The method according to claim 24, wherein at least one tuple of the graph-based data structure is generated as a result of a clinical study.

31. The method according to claim 24, wherein the path comprises at least one tuple having a trust score.

32. The method according to claim 31, wherein a trust score is provided to indicate a likelihood of following the path through the graph-based data structure.

33. The method according to claim 31, wherein the trust score is used to determine the final actionable item node.

34. The method according to claim 24, wherein the traversing is performed at least partially by an inference engine.

35. The method according to claim 24, further comprising an act of displaying an output of the one or more actionable items represented by the final actionable item node to a user of the computer system.

36. The method according to claim 24, wherein the graph-based data structure includes a resource description framework model (RDF).

37. The method according to claim 24, wherein the graph-based data structure includes a plurality of complex data elements.

38. The method according to claim 37, wherein at least one of the plurality of complex data elements includes a text node element that stores information relevant for precision medicine decision making with respect to a referenced element of the graph-based data structure.

39. The method according to claim 37, wherein at least one of the plurality of complex data elements includes a disease therapy association (DTA) element that associates a disease and a therapy with information relevant to a combination of the disease and the therapy.

40. The method according to claim 37, wherein at least one of the plurality of complex data elements includes a therapy genomic effect (TGE) element that associates a gene targeted by a therapy and a known effect of the therapy.

41. The method according to claim 24, wherein each AG of the plurality of AGs comprises a plurality of gene states.

42. The method according to claim 41, wherein each of the plurality of gene states belongs to a single AG.

43. The method according to claim 41, wherein at least one AG of the plurality of AGs comprises a combination of attributes that defines a unique set of clinically relevant gene states.

44. The method according to claim 24, further comprising an act of propagating, by the computer system, information within the graph-based data structure that includes the biomarker data and the patient-specific pathology information.

45. The method according to claim 44, further comprising an act of propagating, by the computer system, an FDA approval status within a disease ontology tree associated with the graph-based data structure.

46. The method according to claim 44, further comprising an act of inferring, by the computer system, relations within the graph-based data structure based on one or more propagation rules.

* * * * *